United States Patent
Altman et al.

(10) Patent No.: US 8,592,425 B2
(45) Date of Patent: Nov. 26, 2013

(54) IMIDAZO[1,2-A]PYRIDINES AND IMIDAZO[1,2-B]PYRIDAZINES AS MARK INHIBITORS

(75) Inventors: Michael D. Altman, Needham, MA (US); Mark T. Bilodeau, Lansdale, PA (US); Jongwon Lim, Lexington, MA (US); Alan Northrup, Reading, MA (US); Matthew G. Stanton, Holland, PA (US); Brandon M. Taoka, Allston, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/144,123

(22) PCT Filed: Jan. 12, 2010

(86) PCT No.: PCT/US2010/020718
§ 371 (c)(1),
(2), (4) Date: Sep. 26, 2011

(87) PCT Pub. No.: WO2010/083145
PCT Pub. Date: Jul. 22, 2010

(65) Prior Publication Data
US 2012/0010209 A1    Jan. 12, 2012

Related U.S. Application Data

(60) Provisional application No. 61/145,226, filed on Jan. 16, 2009.

(51) Int. Cl.
*A01N 43/58* (2006.01)
*A61K 31/50* (2006.01)
*C07D 487/00* (2006.01)

(52) U.S. Cl.
USPC ........................... 514/250; 544/236

(58) Field of Classification Search
USPC ........................... 544/236; 514/250
See application file for complete search history.

(56) References Cited

U.S. PATENT DOCUMENTS

| 6,358,971 | B1 | 3/2002 | Ezquerra-Carrera et al. |
| 7,348,339 | B2 | 3/2008 | Bailey et al. |
| 2005/0176753 | A1* | 8/2005 | Bilodeau et al. .............. 514/303 |
| 2010/0305091 | A1 | 12/2010 | Stanton et al. |

FOREIGN PATENT DOCUMENTS

| WO | 2007085873 A1 | | 8/2007 |
| WO | WO2007/085873 | * | 2/2008 |
| WO | 2009014620 A1 | | 1/2009 |
| WO | 2010017046 A1 | | 2/2010 |

OTHER PUBLICATIONS

Vippagunta et al.*
Co-pending U.S. Appl. No. 13/057,510, National Stage entry of PCT/US2009/051785, filed Jul. 27, 2009.

* cited by examiner

*Primary Examiner* — Paul V. Ward
(74) *Attorney, Agent, or Firm* — Susan L. Hess; Raynard Yuro; John C. Todaro

(57) ABSTRACT

The invention encompasses imidazo[1,2-a]pyridine and imidazo[1,2-b]pyridazine derivatives which selectively inhibit microtubule affinity regulating kinase (MARK) and are therefore useful for the treatment or prevention of Alzheimer's disease. Pharmaceutical compositions and methods of use are also included.

17 Claims, No Drawings

IMIDAZO[1,2-A]PYRIDINES AND IMIDAZO[1,2-B]PYRIDAZINES AS MARK INHIBITORS

BACKGROUND OF THE INVENTION

Alzheimer's disease (AD) is the most common cause of dementia in the elderly and is characterised by a decline in cognitive function, that progresses slowly and results in symptoms such as memory loss and disorientation. Death occurs, on average, 9 years after diagnosis. The incidence of AD increases with age, so that while about 5% of people over the age of 70 are sufferers, this figure increases to 20% of those over 80 years old.

Existing treatments exclusively target the primary symptoms of AD. Diseased neurons may release insufficient or excessive amounts of particular neurotransmitters, and so current drugs are aimed at increasing neurotransmitter levels or at reducing the stimulation of nerve cells by neurotransmitters. Although these drugs provide some improvement in the symptoms of AD, they fail to address the underlying cause of the disease.

The classic clinical and neuropathological features of AD consist of senile or neuritic plaques and tangled bundles of fibers (neurofibrillary tangles) [Verdile, G., et al, Pharm. Res. 50:397-409 (2004)]. In addition, there is a severe loss of neurons in the hippocampus and the cerebral cortex. Neuritic plaques are extracellular lesions, consisting mainly of deposits of β-amyloid peptide (Aβ), surrounded by dystrophic (swollen, damaged and degenerating) neurites and glial cells activated by inflammatory processes. In contrast, neurofibrillary tangles (NFTs) are intracellular clusters composed of a hyperphosphorylated form of the protein tau, which are found extensively in the brain (e.g. mainly in cortex and hippocampus in AD). Tau is a soluble cytoplasmic protein which has a role in microtubule stabilisation. Excessive phosphorylation of this protein renders it insoluble and leads to its aggregation into paired helical filaments, which in turn form NFTs.

The amyloid cascade hypothesis proposes that abnormal accumulation of Aβ peptides, particularly Aβ42, initiates a cascade of events leading to the classical symptoms of AD and ultimately, to the death of the patient. There is strong evidence [e.g. Rapoport, M., et al (2002) Proc. Natl. Acad. Sci. USA 99:6364-6369] that dysregulation of tau function is a key step in the cascade of Alzheimer's disease pathology leading ultimately to neuronal death. Furthermore, tau mutations and NFTs are found in other dementias in which Aβ pathology is absent, such as frontotemporal dementia, Pick's disease and parkinsonism linked to chromosome 17 (FTDP-17) [Mizutani, T. (1999) Rinsho Shikeigaku 39: 1262-1263]. Also, in AD the frequency of NFTs correlates to the degree of dementia better than that of senile plaques [Arriagada, P. V., et al (1992) Neurology 42:631-639], while significant numbers of amyloid plaques are often found in the brains of non-demented elderly people, suggesting that amyloid pathology on its own is not sufficient to cause dementia. For these reasons, normalisation of tau function (in particular prevention of hyperphosphorylation) is seen as a desirable therapeutic goal for the treatment of AD and other dementing conditions.

Tau is a 352-441 amino acid protein encoded by the Mapt (Microtubule-associated protein tau) gene which is widely expressed in the central nervous system (CNS) with localisation primarily in axons [Binder et al J. Cell Biol. 1985, 101(4), 1371-1378]. The major function of tau is regulation of the stability of microtubules (MTs), intracellular structural components comprised of tubulin dimers which are integral in regulating many essential cellular processes such as axonal transport and elongation as well as generation of cell polarity and shape. Tau binding to tubulin is a key factor in determining the rates of polymerisation/depolymerization (termed dynamic instability) of MTs, and tau is therefore key to the regulation of many essential cellular processes [see, for example, Butner, K. A., Kirschner, M. W. (1991) J. Cell. Biol. 115: 717-730].

Tau is a basic protein with numerous serine and threonine residues, many of which are susceptible to phosphorylation. While normal tau has two to three phosphorylated amino acid residues, hyperphosphorylated tau found in AD and other tauopathies typically has eight or nine phosphorylated residues. A variety of kinases promote phosphorylation of these sites, including proline-directed kinases such as glycogen synthase kinase 3β (GSK3β) and cyclin dependent kinase 5 (cdk5), and non-proline-directed kinases such as protein kinase A (PKA) and calmodulin (CaM) kinase II, which phosphorylate tau at Lys-(Ile/Cys)-Gly-Ser sequences, also known as KXGS motifs. One KXGS motif is found in each of the MT binding repeats. Phosphorylation at these sites is important for the regulation of tau-MT binding and while the degree of phosphorylation is normally low, it has been shown to be increased in brain tissue from AD patients. Phosphorylation of one particular residue within the KXGS motifs, Ser-262 has been shown to be elevated in tau protein extracted from the NFTs in AD [Hasegawa, M. et al (1992) J. Biol. Chem. 267:17047-17054] and phosphorylation at this site also appears to dramatically reduce MT binding [Biernat, J. et al. (1993) Neuron 11: 153-163]. Nishimura et al. [Cell 116: 671-682 (2004)] demonstrated that overexpression of the kinase PAR-1 in *Drosophila* led to enhanced tau-mediated toxicity and an increase in the phosphorylation of tau on Ser-262, Ser-356, and other amino acid residues, including sites phosphorylated by GSK3β and Cdk5. Their findings suggest that PAR-1 kinase acts as a master kinase during the process of tau hyperphosphorylation, with the phosphorylation of the Ser-262 and Ser-356 sites being a prerequisite for the subsequent phosphorylation at downstream sites by other kinases.

The mammalian ortholog of PAR-1 is microtubule affinity-regulating kinase (MARK). There are four MARK isoforms and these form part of the AMP-dependent protein kinase (AMPK) family. Like PAR-1, MARK is thought to phosphorylate tau, perhaps in response to an external insult, such as the disruption of $Ca^{2+}$ homeostasis caused by Aβ, priming it for further phosphorylation events. It is not clear whether the phosphorylation of tau by MARK leads directly to its detachment from MTs or the subsequent phosphorylation events cause detachment. The resulting unbound, hyperphosphorylated tau is delocalised to the somatodendritic compartment and is then cleaved by caspases to form fragments prone to aggregation [Drewes, G. (2004). Trends Biochem. Sci 29:548-555; Gamblin, T. C., et al, (2003) Proc. Natl. Acad. Sci. U.S.A. 100:10032-10037]. These aggregates can grow into filaments, which are potentially toxic, eventually forming the NFTs found in AD.

For these reasons, it is proposed that MARK inhibitors will enable the prevention or amelioration of neurodegeneration in AD and other tauopathies.

This invention relates to methods and materials for the treatment or prevention of neurodegenerative diseases such as Alzheimer's disease. In particular, there is disclosed a particular class of imidazo[1,2-a]pyridine and imidazo[1,2-b]

pyridazine derivatives which selectively inhibit microtubule affinity regulating kinase (MARK).

SUMMARY OF THE INVENTION

The invention encompasses imidazo[1,2-a]pyridine and imidazo[1,2-b]pyridazine derivatives which selectively inhibit microtubule affinity regulating kinase (MARK) and are therefore useful for the treatment or prevention of Alzheimer's disease. Pharmaceutical compositions and methods of use are also included.

DETAILED DESCRIPTION OF THE INVENTION

The invention encompasses a genus of compounds of formula I:

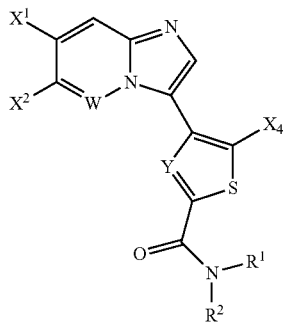

or a pharmaceutically acceptable salt or hydrate thereof; wherein:

W is selected from =N— and =C($X^3$)—;

$X^1$ is selected from the group consisting of: H, halogen, $CF_3$, phenyl, and a monocyclic or bicyclic ring system comprising up to 10 ring atoms, of which 1-3 are selected from N, O and $S(O)_X$ and the remainder are C, said phenyl and ring system bearing 0-3 substituents independently selected from halogen and $C_{1-4}$alkyl, optionally substituted with up to 3 halogen atoms;

$X^2$ is selected from the group consisting of: H, halogen and phenyl bearing 0 to 5 halogen substituents;

$X^3$ is selected from the group consisting of: H, $OR^3$, $N(R^3)_2$, $C_{1-6}$alkyl and halogen;

$X^4$ is selected from the group consisting of H, halogen, phenyl-$(CH_2)_p$—, $C_{3-6}$cycloalkyl-$(CH_2)_q$—, $C_{1-6}$alkyl and $C_{2-6}$alkenyl, said phenyl-$(CH_2)_p$—, $C_{3-6}$cycloalkyl-$(CH_2)_q$—, $C_{1-6}$alkyl and $C_{2-6}$alkenyl optionally substituted with up to 3 halogen atoms, and p and q are independently 0, 1, 2 or 3;

Y is selected from the group consisting of: =N— and =CH—;

$R^1$ represents H or $C_{1-4}$alkyl which is optionally substituted with OH, CN, $CF_3$, $C_{1-4}$alkoxy, amino, $C_{1-4}$alkylamino or di($C_{1-4}$alkyl)amino;

$R^2$ is selected from:

(i) H;

(ii) $C_{1-8}$alkyl or $C_{2-8}$alkenyl, either of which optionally bears up to 3 substituents independently selected from halogen, OH, CN, $CF_3$, $OR^3$, $SR^4$, $SO_2R^4$, $SO_2N(R^3)_2$, $COR^3$, $CO_2R^3$, $CON(R^3)_2$, $N(R^3)_2$, $NR^3COR^4$, $NR^3SO_2R^4$ and phenyl, said phenyl bearing 0 to 5 halogen substituents; and (iii) $C_{3-10}$cycloalkyl, $C_{3-10}$cycloalkyl$C_{1-4}$alkyl, Het, Het$C_{1-4}$alkyl, aryl or aryl$C_{1-4}$alkyl, any of which optionally bears up to 3 substituents independently selected from halogen, OH, oxo, CN, $CF_3$, $R^4$, $OR^3$, $SR^4$, $SO_2R^4$, $SO_2N(R^3)_2$, $COR^3$, $CO_2R^3$, $CON(R^3)_2$, $N(R^3)_2$, $NR^3COR^4$ and $NR^3SO_2R^4$; where "aryl" refers to phenyl or 5- or 6-membered heteroaryl, either of which phenyl or heteroaryl is optionally fused to a 5- or 6-membered carbocycle or heterocycle, and "Het" refers to a nonaromatic mono- or bicyclic heterocyclic system of up to 10 ring atoms, of which 1-3 are selected from N, O and $S(O)_X$ and the remainder are C;

or $R^1$ and $R^2$ together may complete a mono- or bicyclic heterocyclic system of up to 10 ring atoms which optionally bears up to 3 substituents independently selected from halogen, OH, oxo, CN, $CF_3$, $R^4$, $OR^3$, $SR^4$, $SO_2R^4$, $SO_2N(R^3)_2$, $COR^3$, $CO_2R^3$, $CON(R^3)_2$, $N(R^3)_2$, $NR^3COR^4$ and $NR^3SO_2R^4$;

each $R^3$ independently represents H or $C_{1-6}$alkyl which is optionally substituted with up to 3 halogen atoms or with OH, CN, $CF_3$, $C_{1-4}$alkoxy, amino, $C_{1-4}$alkylamino or di($C_{1-4}$alkyl)amino, or $R^3$ represents phenyl, benzyl or 5- or 6-membered heteroaryl, any of which optionally bears up to 3 substituents independently selected from halogen, OH, CN, $CF_3$, $C_{1-4}$alkyl, $C_{1-4}$alkoxy, amino, $C_{1-4}$alkylamino and di($C_{1-4}$alkyl)amino;

or two $R^3$ groups attached to the same nitrogen atom may complete a heterocycle of up to 6 ring atoms which optionally bears up to 3 substituents independently selected from halogen, OH, oxo, CN, $CF_3$, $C_{1-4}$alkyl, $C_{1-4}$alkoxy, amino, $C_{1-4}$alkylamino and di($C_{1-4}$alkyl)amino;

$R^4$ has the same definition as $R^3$ except that $R^4$ is not H; and each x is independently 0, 1 or 2.

Within the genus, the invention encompasses a subgenus of compounds of formula I wherein W is =N—.

Also within the genus, the invention encompasses a subgenus of compounds of formula I wherein W is =C($X^3$)— and $X^3$ is H.

Also within the genus, the invention encompasses a subgenus of compounds of formula I wherein Y is =CH—.

Also within the genus, the invention encompasses a subgenus of compounds of formula I wherein Y is =N—.

Also within the genus, the invention encompasses a subgenus of compounds of formula I wherein $X^1$ is phenyl bearing 0 to 3 halogen substituents.

Also within the genus, the invention encompasses a subgenus of compounds of formula I wherein $X^1$ is H.

Also within the genus, the invention encompasses a subgenus of compounds of formula I wherein $X^1$ is halogen.

Also within the genus, the invention encompasses a subgenus of compounds of formula I wherein $X^1$ is $CF_3$.

Also within the genus, the invention encompasses a subgenus of compounds of formula I wherein $X^2$ is H.

Also within the genus, the invention encompasses a subgenus of compounds of formula I wherein $X^4$ is selected from H, halogen, $C_{1-4}$alkyl bearing 0 to 3 halogen substituents, cyclopropyl, cyclopropylmethyl and benzyl.

Also within the genus, the invention encompasses a subgenus of compounds of formula I wherein $R^1$ is H.

Also within the genus, the invention encompasses a subgenus of compounds of formula I wherein $R^2$ is $C_{3-10}$cycloalkyl bearing up to 3 substituents independently selected from halogen, OH, oxo, CN, $CF_3$, $R^4$, $OR^3$, $SR^4$, $SO_2R^4$, $SO_2N(R^3)_2$, $COR^3$, $CO_2R^3$, $CON(R^3)_2$, $N(R^3)_2$, $NR^3COR^4$ and $NR^3SO_2R^4$. Within this subgenus, the invention encompasses a class of compounds of Formula I wherein $R^2$ is cyclohexyl bearing up to 3 substituents independently selected from halogen, OH, oxo, CN, $CF_3$, $R^4$, $OR^3$, $SR^4$, $SO_2R^4$, $SO_2N(R^3)_2$, $COR^3$, $CO_2R^3$, $CON(R^3)_2$, $N(R^3)_2$, $NR^3COR^4$ and $NR^3SO_2R^4$.

Also within the genus, the invention encompasses a subgenus of compounds of formula I wherein: W is =N—; Y is —CH—; $X^1$ is selected from the group consisting of: H, halogen, phenyl bearing 0 to 3 halogen substituents and $CF_3$; $X^2$ is H; $X^4$ is selected from the group consisting of: H, halogen, $C_{1-4}$alkyl bearing 0 to 3 halogen substituents, cyclopropyl, cyclopropylmethyl and benzyl; $R^1$ is H; and $R^2$ is $C_{3-10}$cycloalkyl, $C_{3-10}$cycloalkyl$C_{1-4}$alkyl, Het, Het$C_{1-4}$alkyl, aryl or aryl$C_{1-4}$alkyl, any of which optionally bears up to 3 substituents independently selected from halogen, OH, oxo, CN, $CF_3$, $R^4$, $OR^3$, $SR^4$, $SO_2R^4$, $SO_2N(R^3)_2$, $COR^3$, $CO_2R^3$, $CON(R^3)_2$, $N(R^3)_2$, $NR^3COR^4$ and $NR^3SO_2R^4$; where "aryl" refers to phenyl or 5- or 6-membered heteroaryl, either of which phenyl or heteroaryl is optionally fused to a 5- or 6-membered carbocycle or heterocycle, and "Het" refers to a nonaromatic mono- or bicyclic heterocyclic system of up to 10 ring atoms, of which 1-3 are selected from N, O and $S(O)_X$ and the remainder are C.

Also within the genus, the invention encompasses a subgenus of compounds of formula I wherein: W is =C($X^3$)— and $X^3$ is H; Y is =CH—; $X^1$ is selected from the group consisting of: H, halogen, phenyl bearing 0 to 3 halogen substituents and $CF_3$; $X^2$ is H; $X^4$ is selected from the group consisting of: H, halogen, $C_{1-4}$alkyl bearing 0 to 3 halogen substituents, cyclopropyl, cyclopropylmethyl and benzyl; $R^1$ is H; and $R^2$ is $C_{3-10}$cycloalkyl, $C_{3-10}$cycloalkyl$C_{1-4}$alkyl, Het, Het$C_{1-4}$alkyl, aryl or aryl$C_{1-4}$alkyl, any of which optionally bears up to 3 substituents independently selected from halogen, OH, oxo, CN, $CF_3$, $R^4$, $OR^3$, $SR^4$, $SO_2R^4$, $SO_2N(R^3)_2$, $COR^3$, $CO_2R^3$, $CON(R^3)_2$, $N(R^3)_2$, $NR^3COR^4$ and $NR^3SO_2R^4$; where "aryl" refers to phenyl or 5- or 6-membered heteroaryl, either of which phenyl or heteroaryl is optionally fused to a 5- or 6-membered carbocycle or heterocycle, and "Het" refers to a nonaromatic mono- or bicyclic heterocyclic system of up to 10 ring atoms, of which 1-3 are selected from N, O and $S(O)_X$ and the remainder are C.

Also within the genus, the invention encompasses a subgenus of compounds of formula I wherein: W is =N—; Y is =N—; $X^1$ is selected from the group consisting of H, halogen, phenyl bearing 0 to 3 halogen substituents and $CF_3$; $X^2$ is H; 4 is selected from the group consisting of: H, halogen, $C_{1-4}$alkyl bearing 0 to 3 halogen substituents, cyclopropyl, cyclopropylmethyl and benzyl; $R^1$ is H; and $R^2$ is $C_{3-10}$cycloalkyl, $C_{3-10}$cycloalkyl$C_{1-4}$alkyl, Het, Het$C_{1-4}$alkyl, aryl or aryl$C_{1-4}$alkyl, any of which optionally bears up to 3 substituents independently selected from halogen, OH, oxo, CN, $CF_3$, $R^4$, $OR^3$, $SR^4$, $SO_2R^4$, $SO_2N(R^3)_2$, $COR^3$, $CO_2R^3$, $CON(R^3)_2$, $N(R^3)_2$, $NR^3COR^4$ and $NR^3SO_2R^4$; where "aryl" refers to phenyl or 5- or 6-membered heteroaryl, either of which phenyl or heteroaryl is optionally fused to a 5- or 6-membered carbocycle or heterocycle, and "Het" refers to a nonaromatic mono- or bicyclic heterocyclic system of up to 10 ring atoms, of which 1-3 are selected from N, O and $S(O)_X$ and the remainder are C.

Also within the genus, the invention encompasses a subgenus of compounds of formula I wherein: W is =C($X^3$)— and $X^3$ is H; Y is =N—; $X^1$ is selected from the group consisting of: H, halogen, phenyl bearing 0 to 3 halogen substituents and $CF_3$; $X^2$ is H; $X^4$ is selected from the group consisting of: H, halogen, $C_{1-4}$alkyl bearing 0 to 3 halogen substituents, cyclopropyl, cyclopropylmethyl and benzyl; $R^1$ is H; and $R^2$ is $C_{3-10}$cycloalkyl, $C_{3-10}$cycloalkyl$C_{1-4}$alkyl, Het, Het$C_{1-4}$alkyl, aryl or aryl$C_{1-4}$alkyl, any of which optionally bears up to 3 substituents independently selected from halogen, OH, oxo, CN, $CF_3$, $R^4$, $OR^3$, $SR^4$, $SO_2R^4$, $SO_2N(R^3)_2$, $COR^3$, $CO_2R^3$, $CON(R^3)_2$, $N(R^3)_2$, $NR^3COR^4$ and $NR^3SO_2R^4$; where "aryl" refers to phenyl or 5- or 6-membered heteroaryl, either of which phenyl or heteroaryl is optionally fused to a 5- or 6-membered carbocycle or heterocycle, and "Het" refers to a nonaromatic mono- or bicyclic heterocyclic system of up to 10 ring atoms, of which 1-3 are selected from N, O and $S(O)_X$ and the remainder are C.

The invention also encompasses a compound selected from the examples described below, including stereoisomers or mixtures thereof, or a pharmaceutically acceptable salt of any of these compounds or stereoisomers.

The invention also encompasses a pharmaceutical composition comprising a compound of formula I or a pharmaceutically acceptable salt or hydrate thereof, and a pharmaceutically acceptable carrier.

The invention further provides a method for treatment or prevention of a neurodegenerative disease associated with hyperphosphorylation of tau in a human patient, said method comprising administering to that patient an effective amount of a compound of formula I as defined above, or a pharmaceutically acceptable salt or hydrate thereof.

Neurodegenerative diseases associated with hyperphosphorylation of tau include AD, frontotemporal dementia, Pick's disease and parkinsonism linked to chromosome 17 (FTDP-17).

In a further aspect, the invention provides a method for reducing the production of hyperphosphorylated tau in a human patient, said method comprising administering to said patient an effective amount of a compound of formula I as defined above or a pharmaceutically acceptable salt or hydrate thereof.

As used herein, the expression "$C_{1-x}$alkyl" where x is an integer greater than 1 refers to straight-chained and branched alkyl groups wherein the number of constituent carbon atoms is in the range 1 to x. Particular alkyl groups are methyl, ethyl, n-propyl, isopropyl and t-butyl. Derived expressions such as "$C_{2-6}$alkenyl", "hydroxy$C_{1-6}$alkyl", "heteroaryl$C_{1-6}$alkyl", "$C_{2-6}$alkynyl" and "$C_{1-6}$alkoxy" are to be construed in an analogous manner. Most suitably, the number of carbon atoms in such groups is not more than 6.

The term "halogen" as used herein includes fluorine, chlorine, bromine and iodine.

The expression "$C_{3-x}$cycloalkyl" as used herein, where x is an integer greater than 3, refers to nonaromatic hydrocarbon ring systems containing from 3 to x ring atoms. Said systems may be monocyclic or bicyclic if the magnitude of x allows it. Examples include cyclopropyl, cyclobutyl, cyclopentyl, cyclohexyl, cycloheptyl, bicycloheptyl and decalinyl.

Unless indicated otherwise, the term "bicyclic" includes bridged bicyclic and spiro-linked ring systems as well as fused ring systems. However, a bicyclic system in which one or both rings are aromatic is of necessity a fused ring system.

For use in medicine, the compounds of formula I may be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, benzenesulphonic acid, fumaric acid, maleic acid, succinic acid, acetic acid, trifluoroacetic acid, benzoic acid, oxalic acid, citric acid, tartaric acid, carbonic acid or phosphoric acid. Alternatively, where the compound of the invention carries an acidic moiety, a pharmaceutically acceptable salt may be formed by neutralisation of said acidic moiety with a suitable base. Examples of pharmaceutically acceptable salts thus formed include alkali metal salts such as sodium or potassium salts; ammonium salts; alkaline earth metal salts such as calcium or magnesium salts; and salts formed with suitable organic bases, such as amine salts (including pyridinium salts) and quaternary ammonium salts.

When the compounds useful in the invention have one or more asymmetric centres, they may accordingly exist as enantiomers. Where the compounds according to the invention possess two or more asymmetric centers, they may additionally exist as diastereoisomers. It is to be understood that all such isomers and mixtures thereof in any proportion are encompassed within the scope of the present invention. Any formulas, structures or names of compounds described herein that do not specify a particular stereochemistry are meant to encompass any and all existing isomers as described above in substantially pure form free of other isomers and mixtures thereof in any proportion. When stereochemistry is specified, the invention is meant to encompass that particular isomer, either in substantially pure form free of other isomers or as part of a mixture.

When a compound useful in the invention is capable of existing in tautomeric keto and enol forms, both of said forms are considered to be within the scope of the invention.

A nitrogen atom forming part of a heteroaryl ring may be in the form of the N-oxide. A sulphur atom forming part of a nonaromatic heterocycle may be in the form of the S-oxide or S,S-dioxide.

A heteroaryl group may be attached to the remainder of the molecule via a ring carbon or a ring nitrogen, provided that this is consistent with preservation of aromaticity.

In formula I, $X^1$ may represent a monocyclic or bicyclic ring system comprising up to 10 ring atoms, of which 1-3 are heteroatoms selected from N, O and $S(O)_x$ and the remainder are C. In the case of a bicyclic system comprising 2 or 3 heteroatoms, said heteroatoms may be confined to one of the rings or distributed over both of the rings. In the case of a bicyclic system, preferably at least one of the rings is aromatic, for example the ring which is bonded to the pyrazolopyridine system of formula I. In the case of a monocyclic system, the ring typically comprises 5 or 6 ring atoms and may be aromatic or nonaromatic, and in a particular embodiment such a ring is either aromatic or partially unsaturated.

Examples of aromatic monocyclic systems represented by $X^1$ include pyridine, pyrazole, imidazole, pyrrole, thiophene and furan.

Examples of nonaromatic monocyclic systems represented by $X^1$ include dihydropyridine and tetrahydropyridine.

Examples of bicyclic systems represented by $X^1$ include indole, benzofuran, quinoline, isoquinoline, 1H-pyrrolo[2,3-b]pyridine, 5,6-dihydro-4H-pyrrolo[1,2-b]pyrazole and 2,3-dihydro-1H-benzimidazole.

It will be apparent to those skilled in the art that a hydroxyl substituent on an unsaturated ring may be capable of tautomerising to a ketone. In such circumstances, both tautomers are to be considered equivalent. Thus, for example, 2-hydroxypyridine is considered equivalent to 2-oxo-1,2-dihydropyridine.

Specific examples of compounds in accordance with the invention are provided in the Examples hereinafter.

It will be apparent to those skilled in the art that individual compounds in accordance with formula I may be converted into other compounds in accordance with formula using standard synthetic techniques. For example, compounds in which $X^1$ is a fluoro-substituted aromatic moiety may be treated with primary or secondary amines in DMF in the presence of alkali at elevated temperatures to provide the corresponding amino-substituted derivatives. Similarly, compounds in which $X^1$ comprises a dihydro- or tetrahydropyridine ring or similar may be N-alkylated using standard methods. Such transformations may also be carried out on intermediates in the synthesis of compounds of formula I.

Where they are not themselves commercially available, the starting materials and reagents described above may be obtained from commercially available precursors by means of well known synthetic procedures and/or the methods disclosed in the Examples section herein.

Where the above-described processes for the preparation of the compounds of use in the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques such as preparative HPLC, or the formation of diastereomeric pairs by salt formation with an optically active acid, such as di-p-toluoyl-D-tartaric acid and/or di-p-toluoyl-L-tartaric acid, followed by fractional crystallization and regeneration of the free base. The compounds may also be resolved by formation of diastereomeric esters or amides, followed by chromatographic separation and removal of the chiral auxiliary During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The compounds of formula I are suitably administered to patients in the form a pharmaceutical composition comprising the active ingredient (i.e. the compound of formula I or pharmaceutically acceptable salt or hydrate thereof) and a pharmaceutically acceptable carrier, and said pharmaceutical compositions constitute a further aspect of the invention.

Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. The principal active ingredient typically is mixed with a pharmaceutical carrier, e.g. conventional tableting ingredients such as corn starch, lactose, sucrose, sorbitol, talc, stearic acid, magnesium stearate and dicalcium phosphate, or gums, dispersing agents, suspending agents or surfactants such as sorbitan monooleate and polyethylene glycol, and other pharmaceutical diluents, e.g. water, to form a homogeneous preformulation composition containing a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. Tablets or pills of the composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions useful in the present invention may be incorporated for administration orally or by injection include aqueous solutions, liquid- or gel-filled capsules, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, poly(ethylene glycol), polyvinylpyrrolidone) or gelatin.

In one embodiment of the invention, the compound of formula I is administered to a patient suffering from AD, FTDP-17, Pick's disease or frontotemporal dementia, in particular AD.

In an alternative embodiment of the invention, the compound of formula I is administered to a patient suffering from mild cognitive impairment or age-related cognitive decline. A favourable outcome of such treatment is prevention or delay of the onset of AD. Age-related cognitive decline and mild cognitive impairment (MCI) are conditions in which a memory deficit is present, but other diagnostic criteria for dementia are absent (Santacruz and Swagerty, *American Family Physician*, 63 (2001), 703-13). (See also "The ICD-10 Classification of Mental and Behavioral Disorders", Geneva: World Health Organisation, 1992, 64-5). As used herein, "age-related cognitive decline" implies a decline of at least six months' duration in at least one of: memory and learning; attention and concentration; thinking; language; and visuospatial functioning and a score of more than one standard deviation below the norm on standardized neuropsychologic testing such as the MMSE. In particular, there may be a progressive decline in memory. In the more severe condition MCI, the degree of memory impairment is outside the range considered normal for the age of the patient but AD is not present. The differential diagnosis of MCI and mild AD is described by Petersen et al., *Arch. Neurol.*, 56 (1999), 303-8. Further information on the differential diagnosis of MCI is provided by Knopman et al, *Mayo Clinic Proceedings*, 78 (2003), 1290-1308. In a study of elderly subjects, Tuokko et al (*Arch, Neurol.*, 60 (2003) 577-82) found that those exhibiting MCI at the outset had a three-fold increased risk of developing dementia within 5 years.

Grundman et al (*J. Mol. Neurosci.*, 19 (2002), 23-28) report that lower baseline hippocampal volume in MCI patients is a prognostic indicator for subsequent AD. Similarly, Andreasen et al (*Acta Neurol. Scand*, 107 (2003) 47-51) report that high CSF levels of total tau, high CSF levels of phospho-tau and lowered CSF levels of Aβ42 are all associated with increased risk of progression from MCI to AD.

Within this embodiment, the compound of formula I is advantageously administered to patients who suffer impaired memory function but do not exhibit symptoms of dementia. Such impairment of memory function typically is not attributable to systemic or cerebral disease, such as stroke or metabolic disorders caused by pituitary dysfunction. Such patients may be in particular people aged 55 or over, especially people aged 60 or over, and preferably people aged 65 or over. Such patients may have normal patterns and levels of growth hormone secretion for their age. However, such patients may possess one or more additional risk factors for developing Alzheimer's disease. Such factors include a family history of the disease; a genetic predisposition to the disease; elevated serum cholesterol; and adult-onset diabetes mellitus.

In a particular embodiment of the invention, the compound of formula I is administered to a patient suffering from age-related cognitive decline or MCI who additionally possesses one or more risk factors for developing AD selected from: a family history of the disease; a genetic predisposition to the disease; elevated serum cholesterol; adult-onset diabetes mellitus; elevated baseline hippocampal volume; elevated CSF levels of total tau; elevated CSF levels of phospho-tau; and lowered CSF levels of Aβ(1-42).

A genetic predisposition (especially towards early onset AD) can arise from point mutations in one or more of a number of genes, including the APP, presenilin-1 and presenilin-2 genes. Also, subjects who are homozygous for the ε4 isofolin of the apolipoprotein E gene are at greater risk of developing AD.

The patient's degree of cognitive decline or impairment is advantageously assessed at regular intervals before, during and/or after a course of treatment in accordance with the invention, so that changes therein may be detected, e.g. the slowing or halting of cognitive decline. A variety of neuropyschological tests are known in the art for this purpose, such as the Mini-Mental State Examination (MMSE) with norms adjusted for age and education (Folstein et al., *J. Psych. Res.*, 12 (1975), 196-198, Anthony et al., *Psychological Med.*, 12 (1982), 397-408; Cockrell et al., *Psychopharmacology*, 24 (1988), 689-692; Crum et al., *J. Am. Med. Assoc'n*. 18 (1993), 2386-2391). The MMSE is a brief, quantitative measure of cognitive status in adults. It can be used to screen for cognitive decline or impairment, to estimate the severity of cognitive decline or impairment at a given point in time, to follow the course of cognitive changes in an individual over time, and to document an individual's response to treatment. Another suitable test is the Alzheimer Disease Assessment Scale (ADAS), in particular the cognitive element thereof (ADAS-cog) (See Rosen et al., *Am. J. Psychiatry*, 141 (1984), 1356-64).

For treating or preventing Alzheimer's disease, a suitable dosage level is about 0.01 to 250 mg/kg per day, preferably about 0.01 to 100 mg/kg per day, and more preferably about 0.05 to 50 mg/kg of body weight per day, of the active compound. The compounds may be administered on a regimen of 1 to 4 times per day. In some cases, however, a dosage outside these limits may be used.

The compound of formula I optionally may be administered in combination with one or more additional compounds known to be useful in the treatment or prevention of AD or the symptoms thereof. Such additional compounds thus include cognition-enhancing drugs such as acetylcholinesterase inhibitors (e.g. donepezil and galanthamine), NMDA antagonists (e.g. memantine) or PDE4 inhibitors (e.g. Ariflo™ and the classes of compounds disclosed in WO 03/018579, WO 01/46151, WO 02/074726 and WO 02/098878). Such additional compounds also include cholesterol-lowering drugs such as the statins, e.g. simvastatin. Such additional compounds similarly include compounds known to modify the production or processing of Aβ in the brain ("amyloid modifiers"), such as compounds which modulate the secretion of Aβ (including γ-secretase inhibitors, γ-secretase modulators and β-secretase inhibitors), compounds which inhibit the aggregation of Aβ, and antibodies which selectively bind to Aβ. Such additional compounds further include growth hormone secretagogues, e.g. as described in WO 2004/080459.

In this embodiment of the invention, the amyloid modifier may be a compound which inhibits the secretion of Aβ, for example an inhibitor of γ-secretase (such as those disclosed in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, WO 2004/089911, WO 02/081435, WO 02/081433, WO 03/018543, WO 2004/031137, WO 2004/031139, WO 2004/031138, WO 2004/101538, WO 2004/101539 and WO 02/47671), or a 3-secretase inhibitor (such as those disclosed in WO 03/037325, WO 03/030886, WO 03/006013, WO 03/006021, WO 03/006423, WO 03/006453, WO 02/002122, WO 01/70672, WO 02/02505, WO 02/02506, WO 02/02512, WO 02/02520, WO 02/098849 and WO 02/100820), or any other compound which inhibits the formation or release of A β including those disclosed in WO 98/28268, WO 02/47671, WO 99/67221, WO 01/34639, WO 01/34571, WO 00/07995, WO 00/38618, WO 01/92235, WO 01/77086, WO 01/74784, WO 01/74796, WO 01/74783, WO 01/60826, WO 01/19797, WO 01/27108, WO 01/27091, WO 00/50391, WO 02/057252, US 2002/0025955 and US2002/0022621, and also including GSK-3 inhibitors, particularly GSK-3α inhibitors, such as lithium, as disclosed in Phiel et al, *Nature*, 423 (2003), 435-9.

Alternatively, the amyloid modifier may be a compound which modulates the action of γ-secretase so as to selectively attenuate the production of Aβ(1-42). Compounds reported to show this effect include certain non-steroidal antiinflammatory drugs (NSAIDs) and their analogues (see WO 01/78721 and US 2002/0128319 and Weggen et al *Nature*, 414 (2001) 212-16; Morihara et al, *J. Neurochem.*, 83 (2002), 1009-12; and Takahashi et al, *J. Biol. Chem.*, 278 (2003), 18644-70), and compounds which modulate the activity of PPARα and/or PPARδ (WO 02/100836). Further examples of γ-secretase modulators are disclosed in WO 2005/054193, WO 2005/013985, WO 2005/108362, WO 2006/008558 and WO 2006/043064.

Alternatively, the amyloid modifier may be a compound which inhibits the aggregation of Aβ or otherwise attenuates is neurotoxicicity. Suitable examples include chelating agents such as clioquinol (Gouras and Beal, *Neuron*, 30 (2001), 641-2) and the compounds disclosed in WO 99/16741, in particular that known as DP-109 (Kalendarev et al, *J. Pharm. Biomed. Anal.*, 24 (2001), 967-75). Other inhibitors of Aβ aggregation suitable for use in the invention include the compounds disclosed in WO 96/28471, WO 98/08868 and WO 00/052048, including the compound known as Apan™ (Praecis); WO 00/064420, WO 03/017994, WO 99/59571 (in particular 3-aminopropane-1-sulfonic acid, also known as tramiprosate or Alzhemed™); WO 00/149281 and the compositions known as PTI-777 and PTI-00703 (ProteoTech); WO 96/39834, WO 01/83425, WO 01/55093, WO 00/76988, WO 00/76987, WO 00/76969, WO 00/76489, WO 97/26919, WO 97/16194, and WO 97/16191. Further examples include phytic acid derivatives as disclosed in U.S. Pat. No. 4,847,082 and inositol derivatives as taught in US 2004/0204387.

Alternatively, the amyloid modifier may be an antibody which binds selectively to Aβ. Said antibody may be polyclonal or monoclonal, but is preferably monoclonal, and is preferably human or humanized. Preferably, the antibody is capable of sequestering soluble Aβ from biological fluids, as described in WO 03/016466, WO 03/016467, WO 03/015691 and WO 01/62801. Suitable antibodies include humanized antibody 266 (described in WO 01/62801) and the modified version thereof described in WO 03/016466. Suitable antibodies also include those specific to Aβ-derived diffusible ligands (ADDLS), as disclosed in WO 2004/031400.

As used herein, the expression "in combination with" requires that therapeutically effective amounts of both the compound of formula I and the additional compound are administered to the subject, but places no restriction on the manner in which this is achieved. Thus, the two species may be combined in a single dosage form for simultaneous administration to the subject, or may be provided in separate dosage forms for simultaneous or sequential administration to the subject. Sequential administration may be close in time or remote in time, e.g. one species administered in the morning and the other in the evening. The separate species may be administered at the same frequency or at different frequencies, e.g. one species once a day and the other two or more times a day. The separate species may be administered by the same route or by different routes, e.g. one species orally and the other parenterally, although oral administration of both species is preferred, where possible. When the additional compound is an antibody, it will typically be administered parenterally and separately from the compound of formula I.

EXAMPLES

MARK 3 Assay

MARK3 activity was assayed in vitro using a Cdc25C biotinylated peptide substrate (Cell Signalling Technologies). The phosphopeptide product was quantitated using a Homogenous Time-Resolved Fluorescence (HTRF) assay system (Park et al., 1999, *Anal. Biochem.* 269:94-104). The reaction mixture contained 50 mM HEPES/Tris-HCl, pH 7.4; mM NaCl, 5 mM MgCl$_2$, 0.2 mM NaVO$_4$, 5 mM 3-glycerol phosphate, 0.1% Tween-20, 2 mM dithiothreitol, 0.1% BSA, 10 μM ATP, 1 μM peptide substrate, and 10 nM recombinant MARK3 enzyme (University of Dundee) in a final volume of 12 μL. The buffer additionally contained protease inhibitor cocktail (Roche EDTA-free, 1 tab per 50 ml). The kinase reaction was incubated for 2 hours at 25° C., and then terminated with 3 μl Stop/Detection Buffer (50 mM HEPES, pH 7.0, 16.6 mM EDTA, 0.5M KF, 0.1% Tween-20, 0.1% BSA, 2 μg/ml SLX$^{ent}$ 665 (CISBIO), and 2 μg/mL Eu$^{3+}$ cryptate label antibody (CISBIO)). The reaction was allowed to equilibrate overnight at 0° C., and relative fluorescent units were read on an HTRF enabled plate reader (e.g. TECAN GENios Pro).

Inhibitor compounds were assayed in the reaction described above to determine compound IC$_{50}$s. Aliquots of compound dissolved in DMSO were added to the reaction wells in a third-log dilution series covering a range of 1 nM to 10 μM. Relative phospho substrate formation, read as HTRF fluorescence units, was measured over the range of compound concentrations and a titration curve generated.

Examples 1 to 29 described herein were tested in the above MARK 3 assay and gave IC$_{50}$ values of 20 μM or less, typically 1 μM or less, and highly active compounds giving values of 100 nM or less. The following table provides IC$_{50}$ values in the above assay for representative examples:

| Example | IC$_{50}$ (nM) |
| --- | --- |
| 1 | 20 |
| 8 | 0.5 |
| 14 | 15 |
| 24 | 140 |
| 29 | 720 | pTau(S262) Cell Biochemical and Functional Assay

The cell biochemical potency of the below described MARK inhibitors was evaluated by measuring their ability to block the phosphorylation of Tau at S262 in primary cell culture of rat cortical neurons induced by the action of Okadaic acid.

Reagents:
  Neurobasal (Invitrogen, cat. 21103-049)
  B27 (Invitrogen, cat. 17504-044)
  L-Glutamine (Invitrogen, cat. 25030-081)
  Penicillin-Streptomycin (Invitrogen, cat. 15140)
  Papain, sterile lyophilized (Worthington, cat. NC9212788) 10 mL 1M Hepes added for 10× solution
  Tissue Culture plates:
    384 well: BD FALCON BD BIOCOAT Poly-D-Lysine Black/Clear Microtest, Tissue-Culture Treated Polystyrene (cat. 354663)
  E18 Primary Rat Cortical Cells: BrainBits, cat. cx2
  Stock Media (NB): Neurobasal+B-27 (1:50)+0.5 mM L-Glutamine+1% Pen/Strep Preparation of Isolated Neurons
  1. Store tissue at 4° C. (1-2 days) until ready to use.
  2. When ready to plate, make up 2 mL of enzymatic solution in Hibernate-Ca containing 1× papain. Filter sterile solution with 0.2 μm filter.
  3. Transfer 2 mL of medium from tissue tube into 15 mL falcon tube while not disturbing tissue. Save media.
  4. Add 2 mL enzymatic media (2) to tissue. Incubate for 30' at 37° C.
  5. Remove enzymatic solution while not disturbing tissue. Add back 1 mL of media from (3).
  6. Using pipettor with sterile plastic tip, triturate ~10 times until most of the cells are dispersed.
  7. Let undispersed pieces settle by gravity 1 minute.
  8. Transfer dispersed cells (supernatant) into 15 mL falcon tube containing 1 mL media from (3). Gently mix cells by swirling.
  9. Spin cells at 1,100 rpm for 1 minute. Remove supernatant.
  10. Flick tube to loosen cell pellet. Resuspend cells in 5 mL of NB.
  11. Transfer to new 50 mL falcon tube using 40 μm cell strainer. Rinse 15 mL falcon tube with 5 mL media, add to strainer.
  12. Count cells using hemacytometer.
  13. Dilute cells to 7,000 cells/100 μL/well in NB.
  14. Incubate cells at 37° C. with 5% CO$_2$.
    a. 4 DIV: Replace ½ volume (50 μL) NB per well.
    b. 6 DIV: Neurite Assay.

Tissue Culture/Compound Treatment
  Primary rat cortical neurons plated @ 6Kcells/well in 384-well black/clear bottom Poly D-Lysine coated BD Falcon Biocoat plates.
    Media: Neurobasal+1× B27+2 mM L-Glutamine (+10% FBS) at time of plating
    Cells maintained at 37° C. and 5% CO$_2$ for *6 days in culture, w/½ media change every 3-4 days.
  Compound treatment:
    Prepare first plate: 200× compound in 100% DMSO with subsequent 3 fold serial dilution
    Prepare intermediate plate: 1:40 dilution of 200× compound in media (2.5% DMSO)
    Add 5× compound to cell in media at 1:5 dilution (0.5% final DMSO)
    Incubate for 30 min. at 37° C.
  Okadaic Acid (OA) Treatment:
    Dilute OA stock (240 μM in 100% DMSO) to 6× final concentration in media (0.5% DMSO)
    Add 6× OA to cells at 1:6 dilution (200 nM final).
  Incubate for 1.5 hrs. at 37° C.
  Fix and Immunostaining
    Fix: 1% PFA, diluted in PBS
    Wash 1× with PBS, residual 30 μl/well.
    Add 30 μL/well warmed 2% PFA and incubate 30 min. at RT (1% PFA final)
    Wash 3× with PBS, 300/well residual
    Permeabilize & Block.
    Add 30 μl/well PBS+0.2% Triton X-100+10% normal goat serum (0.1% Triton & 5% NGS final).
    Incubate 1 hr at RT or O/N at 4° C.
    Wash 3× with PBS, 30 μL/well residual
    Primary antibody: add 30 μL/well 2× final concentration antibody diluted in PBS
      Mouse anti-tau-3R
      Rabbit anti-tau-pS$^{262}$
      Incubate O/N at 4° C.
    Wash 4× with PBS, 30 μL/well residual
    Secondary antibody & nuclear staining: add 30 μl/well 2× final concentration stain diluted in PBS
      AlexaFluor goat anti mouse 488
      AlexaFluor goat anti rabbit 594
      Hoechst
        Incubate in dark 1 hr. at RT
    Wash 4× with PBS 300/well residual, protect from light
    Acquire images in INCell Analyzer 1000 & Opera.

Examples 1 to 29 described herein were tested in the above assay measuring inhibition of phosphorylation of Tau at S262, and examples 1 to 8, 11 to 14, 16 to 18, and 20 to 29 gave 1050 values of 10 μM or less, typically 1,000 nM or less, and highly active compounds giving values of 250 nM or less. Examples 9, 10, 15, and 19 gave IC$_{50}$ values of greater than 10 μM in the above assay.

Methods of Synthesis

The 3-bromoimidazo[1,2-b]pyridazine or 3-bromoimidazo[1,2-a]pyridine A was coupled to the thiophene boronic ester B to afford the coupled product C via Suzuki reaction (Scheme 1). In case of an ester, compound C was hydrolyzed with potassium hydroxide in methanol, and the amide G was formed employing BOP as a coupling reagent. Alternatively, compound C was brominated on the thiophene with thionyl bromide, then a second Suzuki coupling with either potassium alkyltrifluoroborate or boronic ester provided compound F. In case of an ester, compound F was hydrolyzed and coupled with an amine to afford compound H.

Scheme 1

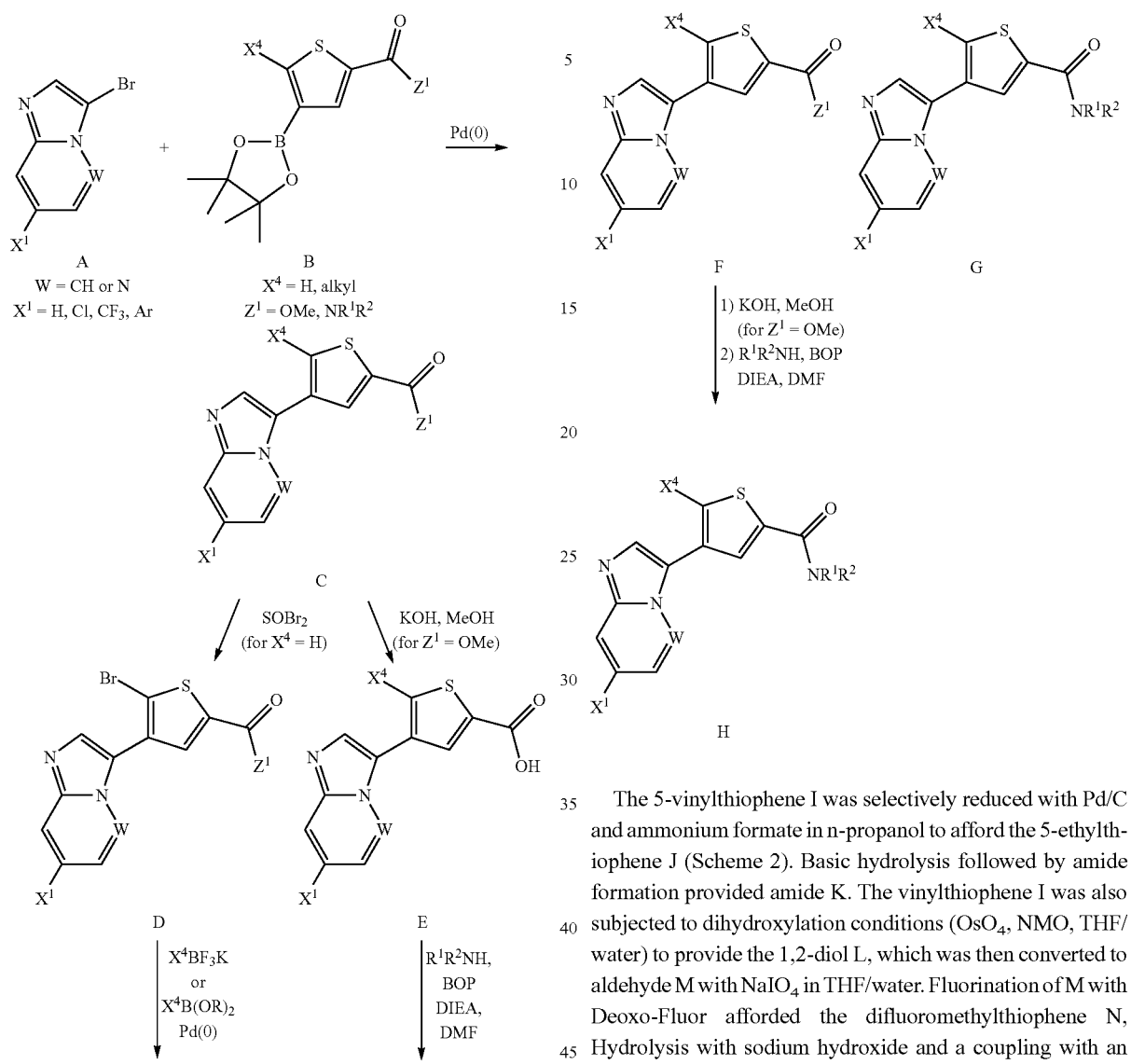

The 5-vinylthiophene I was selectively reduced with Pd/C and ammonium formate in n-propanol to afford the 5-ethylthiophene J (Scheme 2). Basic hydrolysis followed by amide formation provided amide K. The vinylthiophene I was also subjected to dihydroxylation conditions (OsO$_4$, NMO, THF/water) to provide the 1,2-diol L, which was then converted to aldehyde M with NaIO$_4$ in THF/water. Fluorination of M with Deoxo-Fluor afforded the difluoromethylthiophene N, Hydrolysis with sodium hydroxide and a coupling with an amine provided the amide O.

Scheme 2

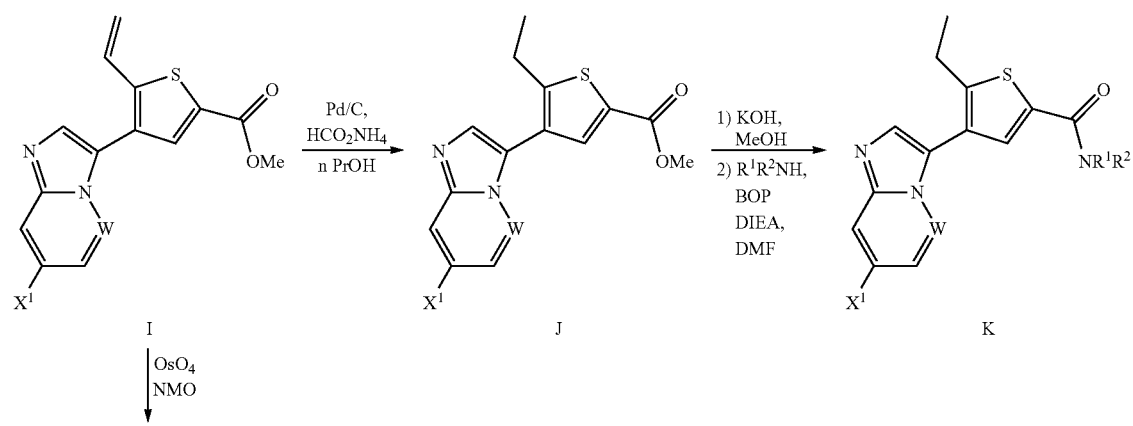

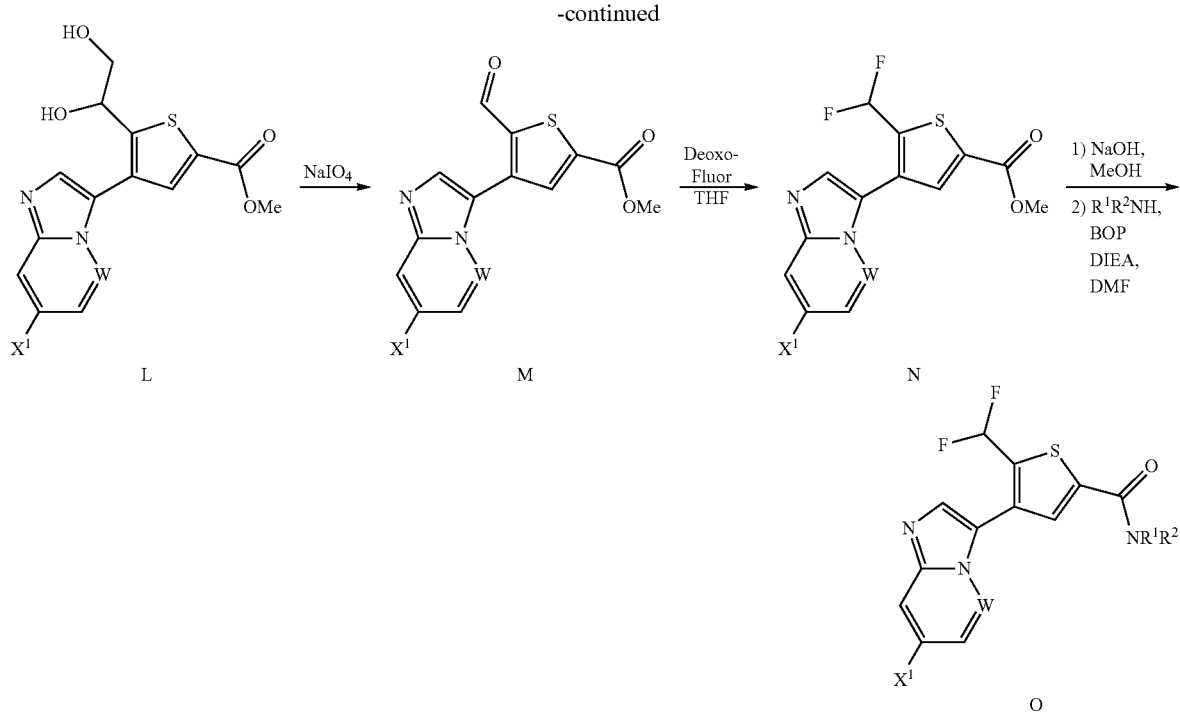

To install the thiazole moiety, the 3-bromoimidazo[1,2-b]pyridazine or 3-bromoimidazo[1,2-a]pyridine A was coupled to tributyl(1-ethoxyvinyl)tin under Stile reaction conditions (Scheme 3). The enol ether was hydrolyzed with aqueous hydrochloric acid to afford ketone P. Bromination with $Br_2$ and HBr afforded the gem-dibromoketone Q, which was then condensed with ethylthiooxamate to provide thiazole R. After basic hydrolysis of the ester, thionyl chloride treatment of compound S at 100° C. converted the acid to the acid chloride and installed a chlorine on the thiazole at the same time. Acid chloride T was coupled with an amine to afford compound U.

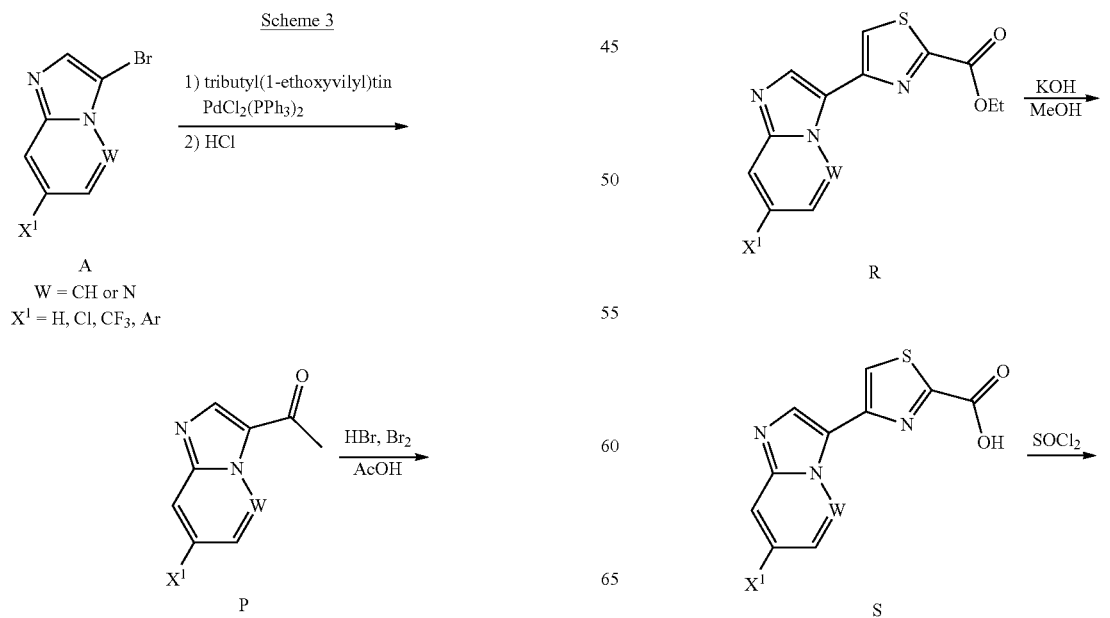

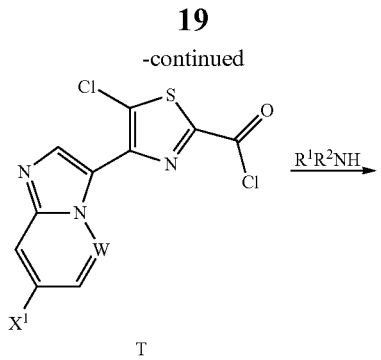

T

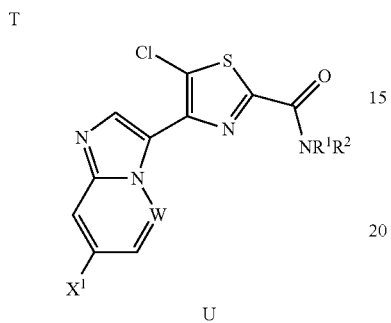

U

Preparation of 3-Bromoimidazo[1,2-B]Pyridazines

The following methods were used to prepare 3-bromoimidazo[1,2-b]pyridazines that were not available from commercial sources or literature.

Intermediate 1

3-Bromo-7-(4-fluorophenyl)imidazo[1,2-b]pyridazine

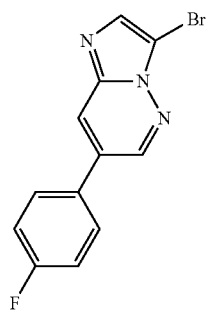

Step 1. 2-Benzyl-4,5-dichloropyridazin-3(2H)-one

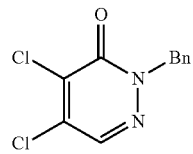 [SMILES: O=c1c(Cl)c(Cl)cnn1Cc1ccccc1]

A stirred mixture of 4,5-dichloropyridazin-3(2H)-one (26.7 g, 160 mmol), benzyl bromide (19.3 mL, 160 mmol), tetrabutylammonium bromide (2.61 g, 8.10 mmol), and potassium carbonate (56.0 g, 405 mmol) in acetonitrile (405 mL) was heated to reflux for 2 h. The mixture was cooled to room temperature, filtered through a fitted glass, concentrated, and purified by flash chromatography to afford the title compound as a white solid. $^1$H NMR (500 MHz, CD$_3$SOCD$_3$) δ 8.23 (s, 1H); 7.27-7.35 (m, 5H); 5.27 (s, 2H). LRMS (APCI) calc'd for (C$_{11}$H$_9$Cl$_2$N$_2$O) [M+H]$^+$, 255.0. found 255.0.

Step 2. 2-Benzyl-5-iodopyridazine-3(2H)-one

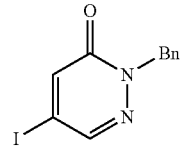 [SMILES: O=c1cc(I)cnn1Cc1ccccc1]

2-Benzyl-4,5-dichloropyridazin-3(2H)-one (32.3 g, 127 mmol) was dissolved in hydriodic acid (223 mL) and the mixture was refluxed at 115° C. overnight. The mixture was poured into dichloromethane and 30% sodium thiosulphate (250 mL), and extracted with dichloromethane (3×250 mL). The combined organics were washed with 30% sodium thiosulphate several times (total 1 L), dried (sodium sulfate), and concentrated. Dichloromethane was added to the residue and the precipitate was collected by filtration to afford the title compound. $^1$H NMR (500 MHz, CD$_3$SOCD$_3$) δ 8.17 (s, 1H); 7.61 (s, 1H); 7.23-7.33 (m, 5H); 5.17 (s, 2H). LRMS (APCI) calc'd for (C$_{11}$H$_{10}$IN$_2$O) [M+H]$^+$, 313.0. found 313.0.

Step 3.
2-Benzyl-5-(4-fluorophenyl)pyridazin-3(2H)-one

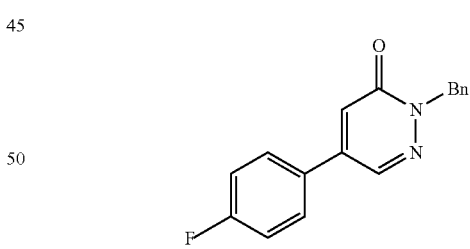

2-Benzyl-5-iodopyridazine-3(2H)-one (5.0 g, 16 mmol), 4-fluorophenyl boronic acid (2.91 g, 20.8 mmol), Pd(Ph$_3$P)$_4$ (0.93 g, 0.80 mmol), and potassium carbonate (6.64 g, 48.1 mmol) were combined in dioxane (120 ml) and Water (40 ml). The reaction mixture was refluxed at 100° C. for 3 h, cooled to room temperature, and poured into ethyl acetate (200 mL) and water (200 mL). The mixture was extracted with ethyl acetate (3×200 mL). The combined organics were washed with water, dried (sodium sulfate), concentrated, and purified by flash chromatography to afford the title compound as a white solid. $^1$H NMR (500 MHz, CD$_3$SOCD$_3$) δ 8.38 (d, 1H);

7.25-7.92 (m, 10H); 5.27 (s, 2H). LRMS (APCI) calc'd for (C₁₇H₁₄FN₂O) [M+H]⁺, 281.1. found 281.1.

Step 4. 5-(4-Fluorophenyl)pyridazin-3(2H)-one

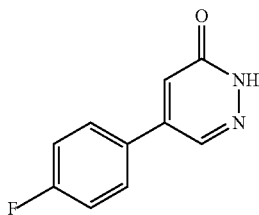

Aluminum chloride (11.4 g, 86 mmol) was added to a stirred mixture of 2-benzyl-5-(4-fluorophenyl)pyridazin-3(2H)-one (4.0 g, 14.3 mmol) in toluene (285 ml) and the mixture was stirred at 70° C. for 1 h. After cooling, the reaction was cooled in an ice bath and quenched slowly with water (50 mL). The precipitate was filtered, washed with water, and dried under high-vacuum to afford the title compound. ¹H NMR (500 MHz, CD₃SOCD₃) δ 8.28 (d, 1H); 7.88 (dd, 2H); 7.35 (t, 2H); 7.13 (d, 1H). LRMS (APCI) calc'd for (C₁₀H₈FN₂O) [M+H]⁺, 191.1. found 191.1.

Step 5. 3-Chloro-5-(4-fluorophenyl)pyridazine

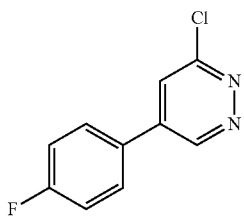 [SMILES: Fc1ccc(-c2cnnc(Cl)c2)cc1]

5-(4-Fluorophenyl)pyridazin-3(2H)-one (2.15 g, 11.3 mmol) was dissolved in POCl₃ (133 ml) and the mixture was refluxed at 110° C. for 30 min. The reaction was cooled in an ice bath and slowly quenched with aqueous sodium hydrogen carbonate (200 mL). The mixture was extracted with ethyl acetate (3×200 mL). The combined organics were washed with water and brine, dried over anhydrous MgSO₄, filtered, and concentrated under reduced pressure to afford the title compound. ¹H NMR (500 MHz, CD₃SOCD₃) δ 9.67 (d, 1H); 8.28 (d, 1H); 8.07 (dd, 2H); 7.42 (t, 2H).

Step 6. 2-{[5-(4-Fluorophenyl)pyridazin-3-yl]amino}ethanol

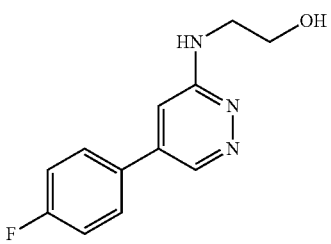 [SMILES: OCCNc1cc(-c2ccc(F)cc2)cnn1]

Ethanolamine (4.82 mL, 80 mmol) was added to a stirred mixture of 3-chloro-5-(4-fluorophenyl)pyridazine (2.08 g, 9.97 mmol) in Dioxane (40 mL) in a sealed tube. The mixture was heated to 120° C. overnight, treated with additional ethanolamine (1.2 mL, 20 mmol), and heated to 150° C. for 2 h. The mixture was cooled and poured into ethyl acetate (100 mL) and water (100 mL). The precipitate was filtered and dried to afford the title compound. ¹H NMR (500 MHz, CD₃SOCD₃) δ 8.76 (d, 1H); 7.78 (dd, 2H); 7.36 (t, 2H); 7.02 (d, 1H); 6.85 (t, 1H); 4.78 (t, 1H); 3.58 (q, 2H); 3.45 (q, 2H). LRMS (APCI) calc'd for (C₁₂H₁₃FN₃O) [M+H]⁺, 234.1. found 234.1.

Step 7. 7-(4-Fluorophenyl)imidazo[1,2-b]pyridazine

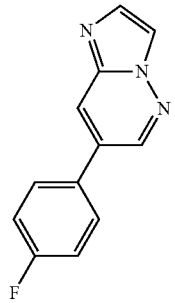 [SMILES: Fc1ccc(-c2cnn3ccnc3c2)cc1]

Oxalyl chloride (3.33 mL, 38.1 mmol) was slowly added to a stirred mixture of DMSO (2.70 mL, 38.1 mmol) in Dichloromethane (25 mL) at −78° C. The mixture was stirred at −78° C. for 10 min before 2-{[5-(4-fluorophenyl)pyridazin-3-yl]amino}ethanol (888 mg, 3.81 mmol) in 3.5 mL DMSO was added. The reaction mixture was left to stir at −78° C. for 20 min, treated with triethylamine (5.31 ml, 38.1 mmol), left to stir at −78° C. for 10 min, and allowed to warm to room temp. The mixture was treated with isopropanol (9 mL), diluted with ethyl acetate (200 mL), and washed with 2% sodium hypochlorite (200 mL) and water (200 mL). The aqueous layer was extracted with chloroform:isopropanol (3:1). The combined organics were dried over anhydrous MgSO₄, filtered, and concentrated under reduced pressure to afford the title compound. LRMS (APCI) calc'd for (C₁₂H₉FN₃) [M+H]⁺, 214.1. found 214.0.

Step 8.
3-Bromo-7-(4-fluorophenyl)imidazo[1,2-b]pyridazine

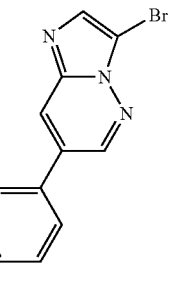

Bromine (0.12 mL, 2.34 mmol) was added dropwise to a stirred mixture of 7-(4-fluorophenyl)imidazo[1,2-b]pyridazine (500 mg, 2.34 mmol) and sodium acetate (289 mg, 3.52 mmol) in Acetic Acid (12 mL) and the mixture was stirred at room temperature for 1 h. The mixture was poured into ethyl acetate and aqueous sodium hydrogen carbonate (50 mL) and extracted with ethyl acetate (3×50 mL). The combined organics were washed with water, dried over anhydrous $MgSO_4$, filtered, and concentrated under reduced pressure. The residue was purified by flash chromatography to afford the title compound as a white solid. $^1$H NMR (500 MHz, $CD_3SOCD_3$) δ 9.10 (d, 1H); 8.49 (d, 1H); 7.98 (dd, 2H); 7.96 (s, 1H); 7.38 (t, 2H). LRMS (APCI) calc'd for ($C_{12}H_8BrFN_3$) [M+H]$^+$, 292.0. found 292.0.

Intermediate 2

3-Bromo-7-(trifluoromethyl)imidazo[1,2-b]pyridazine

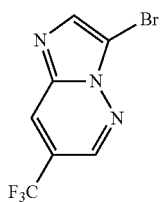

Step 1. 3-Chloro-5-(trifluoromethyl)pyridazine

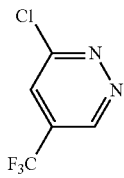

5-(Trifluoromethyl)pyridazin-3(2H)-one (20.0 g, 111 mmol) was dissolved in 1,4-dioxane (222 mL) and $POCl_3$ (31.0 mL, 333 mmol) added. The reaction was left to stir at 80° C. for 3 h. After consumption of the starting material, the reaction was cooled to room temperature. The reaction mixture was added to ice and quenched with ammonium hydroxide. The aqueous layer was extracted with dichloromethane (×3) and the organic layers combined, dried with magnesium sulfate, filtered, and concentrated under reduced pressure. The residue was purified by flash chromatography to afford the title compound as an orange oil. $^1$H NMR (500 MHz, $CDCl_3$) δ 9.37 (s, 1H); 7.76 (s, 1H).

Step 2. 5-(Trifluoromethyl)pyridazin-3-amine

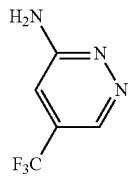

3-Chloro-5-(trifluoromethyl)pyridazine (28.0 g, 153 mmol) was dissolved in ammonia in isopropanol (200 mL, 400 mmol, 2.0 M) and heated at 80° C. in a pressure vessel for 3 days. The reaction was cooled to room temperature and concentrated under reduced pressure to take the isopropanol off. The residue was purified by flash chromatography to afford the title compound as an off white solid, $^1$H NMR (500 MHz, $CDCl_3$) δ 8.83 (s, 1H); 6.91 (s, 1H); 5.00 (s, 2H, br). LRMS (APCI) calc'd for ($C_5H_4F_3N_3$) [M+H]$^+$, 164.1. found 164.1.

Step 3. 7-(Trifluoromethyl)imidazo[1,2-b]pyridazine

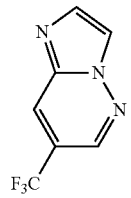 [SMILES: FC(F)(F)c1cnn2ccnc2c1]

5-(Trifluoromethyl)pyridazin-3-amine (6.79 g, 41.6 mmol) was dissolved in a mixture of ethanol (133 mL) and water (33.3 mL) and 50% aq. solution of chloroacetylaldehyde (26.9 mL, 208 mmol) and sodium bicarbonate (17.5 g, 208 mmol) was added. The reaction was sealed in a pressure vessel and heated to 130° C. for 6 h. The reaction was then cooled to room temperature. Water was added and the mixture filtered through celite. The aqueous layer was extracted with a 3:1 mixture of $CHCl_3$:Isopropanol (×3). The organic layers were collected, dried with magnesium sulfate, filtered, and concentrated under reduced pressure. The residue was purified by flash chromatography to afford the title compound as an orange solid. $^1$H NMR (500 MHz, $CDCl_3$) δ 8.52 (s, 1H); 8.27 (s, 1H); 8.13 (s, 1H); 7.97 (s, 1H). LRMS (APCI) calc'd for ($C_7H_4F_3N_3$) [M+H]$^+$, 187.1. found 187.1.

Step 4,3-Bromo-7-(trifluoromethyl)imidazo[1,2-b]pyridazine

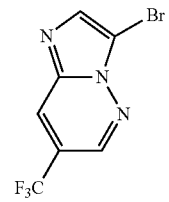

7-(Trifluoromethyl)imidazo[1,2-b]pyridazine (4.32 g, 23.1 mmol) was dissolved in acetic acid (46 mL) and bromine (1.31 mL, 25.4 mmol) added dropwise. The mixture was stirred at room temperature for 1 h. After the reaction was complete, ice was added and the reaction quenched with ammonium hydroxide. The aqueous layer was extracted with ethyl acetate (×3). The organic layers were combined, dried with magnesium sulfate, filtered, and concentrated under reduced pressure. The residue was purified by column chromatography to afford the title compound as a yellow solid. $^1$H NMR (500 MHz, $CDCl_3$) δ 8.65 (s, 1H); 8.25 (s, 1H); 7.98 (s, 1H). LRMS (APCI) calc'd for ($C_7H_3BrF_3N_3$) [M+H]$^+$, 266.0. found 266.0.

Preparation of
[5-(Methoxycarbonyl)Thiophen-3-yl]Boronic Esters

The following methods were used to prepare [5-(methoxycarbonyl)thiophen-3-yl]boronic esters that were not available from commercial sources or literature.

Intermediate 3

Methyl 5-methyl-4-(4,4,5,5-tetramethyl-1,3,2-dioxaborolan-2-yl)thiophene-2-carboxylate

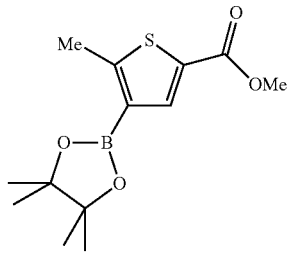 [SMILES: COC(=O)c1cc(B2OC(C)(C)C(C)(C)O2)c(C)s1]

Step 1. Methyl 4-bromo-5-methylthiophene-2-carboxylate

To a stirred solution of 4-bromo-5-methylthiophene-2-carboxylic acid (45 g, 204 mmol) in methanol (225 mL) was added concentrated $H_2SO_4$ (4.0 g, 41 mmol). The reaction mixture was heated to reflux overnight, cooled to room temperature, poured into saturated $NaHCO_3$ (800 mL), and left to stir for 30 min. The precipitate was filtered, washed with water, and dried under high-vacuum to afford the title compound. $^1$H NMR (500 MHz, CDCl$_3$) δ 7.61 (s, 1H); 3.88 (s, 3H); 2.45 (s, 3H). LRMS (APCI) calc'd for ($C_7H_8BrO_2S$) [M+H]$^+$, 234.9. found 234.9.

Step 2. Methyl 5-methyl-4-(4,4,5,5-tetramethyl-1,3,2-dioxaborolan-2-yl)thiophene-2-carboxylate

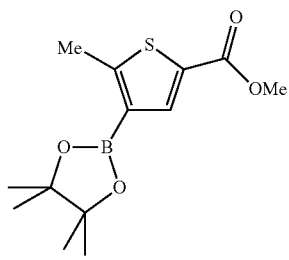 [SMILES: COC(=O)c1cc(B2OC(C)(C)C(C)(C)O2)c(C)s1]

A mixture of methyl 4-bromo-5-methylthiophene-2-carboxylate (47.6 g, 202 mmol), 4,4,4',4',5,5,5',5'-octamethyl-2,2'-bi-1,3,2-dioxaborolane (77 g, 304 mmol), and potassium acetate (59.6 g, 607 mmol) in dioxane (300 mL) was evacuated and flushed with nitrogen twice. DPPF (3.37 g, 6.07 mmol) and 1,1'-bis(diphenylphosphino)ferrocene-palladium (II) dichloride dichloromethane complex (4.96 g, 6.07 mmol) were added to the reaction, and the resultant mixture was evacuated and flushed with nitrogen twice. The mixture was heated at 85° C. for 2 days, cooled to room temperature, and poured into a mixture of water (2 L) and EtOAc (1 L). The organic layer was washed with water and brine, dried over magnesium sulfate, concentrated, and purified by flash chromatography to afford the title compound. $^1$H NMR (500 MHz, CDCl$_3$) δ 7.96 (s, 1H); 3.86 (s, 3H); 2.73 (s, 3H). LRMS (APCI) calc'd for ($C_{13}H_{20}BO_4S$) [M+H]$^+$, 283.1. found 283.1.

According to Intermediate 3, the following [5-(methoxycarbonyl)thiophen-3-yl]boronic ester was prepared from the corresponding 4-bromothiophene-2-carboxylic acid:

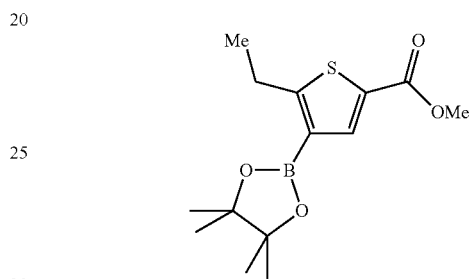

Methyl 5-ethyl-4-(4,4,5,5-tetramethyl-1,3,2-dioxaborolan-2-yl)thiophene-2-carboxylate Preparation of Amines The following methods were used to prepare amines that were not available from commercial sources or literature.

Intermediate 4 tert-Butyl[(1R,2R)-2-amino-3,3-difluorocyclohexyl]carbamate

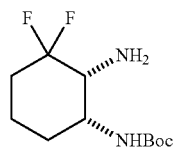 [SMILES: CC(C)(C)OC(=O)N[C@@H]1CCCC(F)(F)[C@@H]1N]

Step 1. 2,2-Difluoro-7-oxabicyclo[4.1.0]heptane

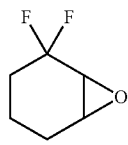

To a solution of 7-oxabicyclo[4.10]heptan-2-one (55.8 g, 0.5 mol) in dichloromethane (200 mL) cooled to 0° C. was added 1,1,1-trifluoro-N,N-bis(2-methoxyethyl)silanamine (Deoxofluor, 202 mL, 1.1 mol) and the resulting reaction was warmed to ambient temperature and stirred for 16 hours. The reaction was cooled to −20° C. and carefully quenched with water (10 mL, slow addition). The reaction was then partitioned between water/dichloromethane and the organics were passed through a plug of silica gel. This crude organic solution of the title compound was carried into the next reaction.

Step 2. (1S,6R)-2,2-Difluoro-6-{[(1R)-1-phenylethyl]amino}cyclohexanol

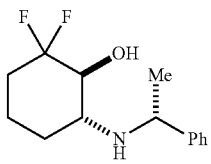 [SMILES: C[C@@H](N[C@@H]1CCCC(F)(F)[C@H]1O)c1ccccc1]

A solution of (1R)-1-phenylethanamine (72 mL, 0.57 mol) in dichloromethane (200 mL) was cooled to 0° C. and treated with trimethylaluminum (260 mL, 0.52 mol) and the resulting solution was stirred for 1 hour at 0° C. To this solution was added a solution of 2,2-difluoro-7-oxabicyclo[4.1.0]heptane (66 g, 0.49 mol) in dichloromethane (200 mL) and the resulting mixture stirred at 0° C. for 3 hours. The reaction was then warmed to ambient temperature for 16 hours. The reaction was cooled to 0° C., treated with 103 g of sodium fluoride and then quenched with water (90 mL, slow addition). The reaction was warmed to ambient temperature, the solids filtered and the solution evaporated in vacuo. Purification by flash chromatography afforded the title compound as a white solid: $^1$H NMR (500 MHz, CDCl$_3$) δ 7.32 (s, 5H); 3.90 (q, 1H); 3.39 (ddd, 1H); 2.70 (m, 1H); 2.11 (m, 1H); 1.80 (m, 1H); 1.62 (m, 2H); 1.43 (m, 1H); 1.36 (d, 3H); 0.96 (m, 1H).

Step 3. (1S,6R)-6-Amino-2,2-difluorocyclohexanol

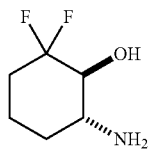

A solution of (1S,6R)-2,2-difluoro-6-{[(1R)-1-phenylethyl]amino}cyclohexanol (2.0 g, 7.8 mmol) in methanol (100 mL) was degassed with nitrogen, treated with Pd(OH)$_2$/C (0.55 g) and then placed under an atmosphere of hydrogen and stirred vigorously for 16 hours. The reaction was filtered, washed with methanol, and the filtrate evaporated in vacuo to afford the title compound as a white solid: $^1$H NMR (500 MHz, CD$_3$OD) δ 3.34 (m, 1H); 2.74 (m, 1H); 2.07 (m, 1H); 1.89 (m, 1H); 1.73 (m, 2H); 1.50 (m, 1H); 1.27 (m, 1H).

Step 4. tert-Butyl[(1R,2S)-3,3-difluoro-2-hydroxycyclohexyl]carbamate

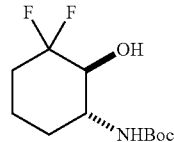

A solution of (1S,6R)-6-amino-2,2-difluorocyclohexanol (2.0 g, 7.54 mmol) in dichloromethane (60 mL) was treated with triethylamine (5.26 mL, 37.7 mmol) and Boc anhydride (1.81 g, 8.30 mmol) and the resulting solution was stirred at ambient temperature for 16 hours. The reaction was evaporated in vacuo and purified by flash chromatography to afford the title compound as a white solid: $^1$H NMR (500 MHz, CDCl$_3$) δ 4.67 (br s, 1H); 3.67 (m, 1H); 3.50 (m, 1H); 3.21 (br s, 1H); 2.15 (m, 1H); 2.03 (m, 1H); 1.62 (m, 3H); 1.45 (s, 9H); 1.34 (m, 1H).

Step 5. (1S,6R)-6-[(tert-Butoxycarbonyl)amino]-2,2-difluorocyclohexyl trifluoromethanesulfonate

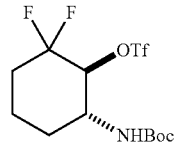 [SMILES: CC(C)(C)OC(=O)N[C@@H]1CCCC(F)(F)[C@H]1OS(=O)(=O)C(F)(F)F]

A solution of text-butyl[(1R,6S)-3,3-difluoro-2-hydroxycyclohexyl]carbamate (1.78 g, 7.08 mmol) in dichloromethane (50 mL) was treated with pyridine (12.5 mL) and cooled to 0° C. Triflic anhydride (4.43 mL, 26.2 mmol) was added dropwise and the reaction was stirred at 0° C. for 2 hours and quenched with water. The reaction was partitioned between water and ether, the organics were dried over sodium sulfate, filtered and evaporated in vacuo. Purification by flash chromatography afforded the title compound as a white solid: $^1$H NMR (500 MHz, CDCl$_3$) δ 4.77 (m, 1H); 4.69 (d, 1H); 3.92 (m, 1H); 2.28 (m, 1H); 2.08 (m, 1H); 1.79 (m, 2H); 1.64 (m, 2H); 1.45 (s, 9H).

Step 6. tert-Butyl[(1R,2R)-2-azido-3,3-difluorocyclohexyl]carbamate

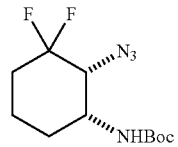 [SMILES: CC(C)(C)OC(=O)N[C@@H]1CCCC(F)(F)[C@@H]1N=[N+]=[N-]]

is A solution of (1S,6R)-6-[(tert-butoxycarbonyl)amino]-2,2-difluorocyclohexyl trifluoromethanesulfonate (2.32 g, 6.05 mmol) and sodium azide (2.36 g, 36.3 mmol) in DMF was sealed and heated to 100° C. for 3 hours in a microwave reactor. The reaction was partitioned between water and ethyl acetate. The organics were washed with water, dried over magnesium sulfate, filtered and evaporated in vacuo. Purification by flash chromatography afforded the title compound as a white solid: $^1$H NMR (500 MHz, CDCl$_3$) δ 4.75 (m, 1H); 3.98 (br s, 1H); 3.88 (m, 1H); 1.96 (m, 2H); 1.70 (m, 2H); 1.46 (s, 9H); 1.37 (m, 2H). tert-Butyl[(1R,6S)-6-azido-2,2-difluorocyclohexyl]carbamate was also obtained from this procedure: $^1$H NMR (500 MHz, CDCl$_3$) δ 4.82-4.80 (d, 1H); 3.93-3.89 (dt, 1H); 3.31-3.27 (m, 1H); 2.24-2.19 (m, 1H); 2.13-2.10 (m, 1H); 1.86-1.67 (m, 2H); 1.55-1.52 (m, 2H); 1.48-1.41 (m, 11H). $^{19}$F NMR (CDCl$_3$, 564 MHz) δ −102.2--102.7 (d, 1F); −113.9--114.5 (m, 1F).

Step 7. tert-Butyl[(1R,2R)-2-amino-3,3-difluorocyclohexyl]carbamate

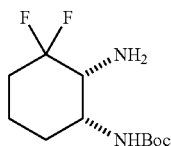 [SMILES: CC(C)(C)OC(=O)N[C@@H]1CCCC(F)(F)[C@@H]1N]

A solution of tert-butyl[(1R,6R)-2-azido-3,3-difluorocyclohexyl]carbamate (0.94 g, 3.40 mmol) in methanol (20 mL) was degassed with nitrogen and treated with 10% Pd/C (72 mg). The resulting heterogenous solution was exposed to a hydrogen atmosphere and stirred vigorously for 16 hours. The reaction was filtered, washed with methanol, and the filtrate evaporated in vacuo to afford the title compound as a white solid: $^1$H NMR (500 MHz, CD$_3$SOCD$_3$) δ 6.67 (d, 1H); 3.55 (br s, 1H); 3.07 (br s, 1H); 2.03 (m, 1H); 1.62 (m, 3H); 1.45 (m, 1H); 1.36 (m, 12H).

Intermediate 5 tert-Butyl[(1S,2R)-2-amino-3,3-difluorocyclohexyl]carbamate

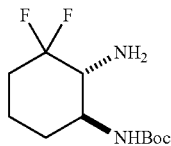 [SMILES: CC(C)(C)OC(=O)N[C@H]1CCCC(F)(F)[C@@H]1N]

Step 1. tert-Butyl[(1R,6S)-6-amino-2,2-difluorocyclohexyl]carbamate

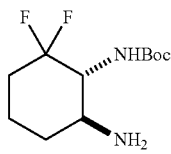

A solution of tert-butyl[(1R,6S)-6-azido-2,2-difluorocyclohexyl]carbamate (18.84 g, 68.2 mmol) in methanol (400 mL) was degassed and purged (3× with N$_2$) before the addition of Pd/C (1.45 g). The reaction was stirred for 2 d under 1 atm of hydrogen. Upon reaction completion, the reaction was filtered through a plug of celite and concentrated to dryness to afford the title compound as a white solid. $^1$H NMR (CDCl3, 500 MHz) δ 4.76-4.74 (d, 1H); 3.61-3.56 (m, 1H); 2.63-2.59 (dd, 1H); 2.2-2.0 (m, 2H); 1.8-1.68, (m, 2H); 1.53-1.42 (m, 11H); 1.29-1.21 (m, 2H). $^{19}$F NMR (CDCl$_3$, 564 MHz) δ −101.7--102.1 (d, 1F); −114.3--114.9 (m, 1F).

Step 2,
(1S,2R)-3,3-Difluorocyclohexane-1,2-diaminium bis(trifluoroacetate)

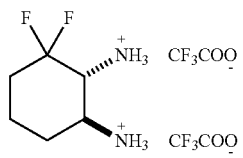

A mixture of tert-butyl[(1R,6S)-6-amino-2,2-difluorocyclohexyl]carbamate (5 g, 19.98 mmol) and TFA (6.16 mL, 80 mmol) in dichloromethane (50 mL) was left to stir overnight, and concentrated to afford the title compound as a brown oil. $^{19}$F NMR (CDCl$_3$, 564 MHz) δ −81.07 (s, 6F); −99.7--100.1 (d, 1F); −111.1--111.5 (d, 1F).

Step 3. tert-Butyl[(1S,2R)-2-amino-3,3-difluorocyclohexyl]carbamate

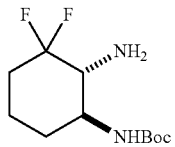

To a stirred solution of (1S,2R)-3,3-difluorocyclohexane-1,2-diaminium bis(trifluoroacetate) (7.5 g, 19.8 mmol) in dichloromethane (100 mL) was added triethylamine (11.1 mL, 79.0 mmol) followed by BOC$_2$O (5.52 mL, 23.8 mmol). The reaction was stirred for 10 hr at ambient temperature. Concentrated, and purified by flash chromatography to afford the title compound. $^1$H NMR (CDCl$_3$, 500 MHz) δ 4.76 (br s, 1H); 3.39 (m, 1H); 2.71-2.64 (m, 1H); 2.2-2.1 (m, 2H); 1.7-1.59 (m, 2H); 1.56-1.51 (m, 2H); 1.45 (s, 9H); 1.29-1.21 (m, 2H). $^{19}$F NMR (CDCl$_3$, 564 MHz) δ −100.4--100.9 (d, 1F); −114.35--114.87 (d, 1F).

Intermediate 6

9H-Fluoren-9-ylmethyl[(1S,2R)-2-amino-3,3-difluorocyclohexyl]carbamate

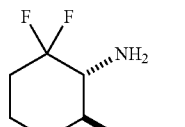

Step 1. tert-Butyl 9H-fluoren-9-ylmethyl[(1S,2R)-3,3-difluorocyclohexane-1,2-diyl]biscarbamate

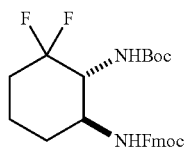

To a slurry of tert-butyl[(1R,6S)-6-amino-2,2-difluorocyclohexyl]carbamate (48 g, 192 mmol) and NaHCO$_3$ (32.2 g, 384 mmol) in acetonitrile (500 mL) and water (500 mL) was slowly added FmocCl in acetonitrile (300 mL) over 1.5 h. To the slurry was added water (500 mL) and the solid was filtered off and washed with water (250 mL) and hexane (500 mL), then dried under high-vacuum to afford the title compound. $^1$H NMR (CDCl$_3$, 400 MHz) δ 7.75 (d, 2H); 7.56 (d, 2H); 7.37 (m, 2H); 7.27 (m, 2H); 5.38 (d, 1H); 5.00 (d, 1H); 4.75 (s, 1H); 4.31 (m, 1H); 4.15 (m, 1H); 4.60-4.85 (m, 2H); 1.25-2.20 (series of m, 6H); 1.36 (s, 9H).

Step 2. (1R,6S)-6-{[(9H-Fluoren-9-ylmethoxy)carbonyl]amino}-2,2-difluorocyclohexanaminium chloride

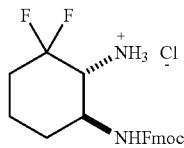

To a slurry of tert-butyl 9H-fluoren-9-ylmethyl[(1S,2R)-3,3-difluorocyclohexane-1,2-diyl]biscarbamate (90 g, 190 mmol) in doixane (500 ml) was added 250 mL of 4 N HCl in dioxane. The solution was warmed to 50° C. for 2 h. Hexanes (600 mL) was added to the warm slurry over 15 min, then the mixture was cooled to 15° C. The precipitate was filtered, washed with hexanes (400 mL), and dried under high-vacuum to afford the title compound.

EXAMPLES

Example 1

N-[(1R,6R)-6-Amino-2,2-difluorocyclohexyl]-4-(imidazo[1,2-b]pyridazin-3-yl)-5-methylthiophene-2-carboxamide

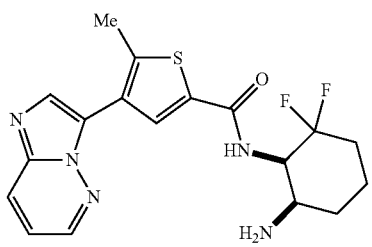

Step 1. 3-Bromoimidazo[1,2-b]pyridazine

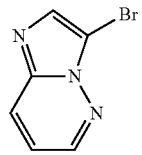

Bromine (0.649 mL, 12.6 mmol) was added dropwise to a stirred mixture of Imidazo[1,2-b]pyridazine (1.0 g, 8.39 mmol) in acetic acid (42 ml) and the mixture was stirred at room temperature for 1 h. The mixture was neutralized with 1 N sodium hydroxide (100 mL) and solid sodium hydroxide, poured into ethyl acetate and sodium bicarbonate solution, and extracted with ethyl acetate (3×200 mL). The combined organics were washed with brine, dried (MgSO$_4$), and concentrated to afford the title compound. $^1$H NMR (600 MHz, CD$_3$SOCD$_3$) δ 8.66 (d, 1H); 8.17 (d, 1H); 7.93 (s, 1H); 7.31 (dd, 1H). LRMS (APCI) calc'd for (C$_6$H$_5$BrN$_3$) [M+H]$^+$, 198.0. found 198.0.

Step 2. Methyl 4-(imidazo[1,2-b]pyridazin-3-yl)-5-methylthiophene-2-carboxylate

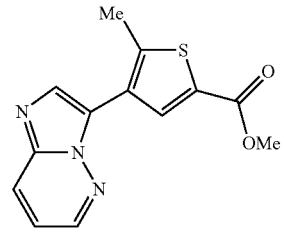 [SMILES: COC(=O)c1cc(-c2cnc3cccnn23)c(C)s1]

3-Bromoimidazo[1,2-b]pyridazine (0.40 g, 2.02 mmol), methyl-5-methyl-3-(4,4,5,5-tetramethyl-1,3,2-dioxaborolan-2-yl)thiophene-2-carboxylate (0.86 g, 3.03 mmol), Pd$_2$(dba)$_3$ (0.19 g, 0.20 mmol), tricyclohexylphosphine (0.14 g, 0.51 mmol), aqueous tribasic potassium phosphate (1.27 M, 1.45 mL, 6.85 mmol), and 1,4-dioxane (10.1 mL) were placed in a flask and purged with nitrogen for five minutes. The solution was heated to 100° C. for four hours. The solution was cooled to room temperature, poured into an aqueous solution of saturated sodium bicarbonate, and extracted with ethyl acetate (×3). The combined organic layers were dried with magnesium sulfate, filtered, and concentrated and the residue purified by flash chromatography to afford the title compound as a yellow solid. $^1$H NMR (500 MHz, CD$_3$SOCD$_3$) δ 8.62 (d, 1H); 8.24 (s, 1H); 8.21 (d, 1H); 8.06 (s, 1H); 7.30 (dd, 1H); 3.83 (s, 3H); 2.58 (s, 3H). LRMS (APCI) calc'd for (C$_{13}$H$_{11}$N$_3$O$_2$S) [M+H]$^+$, 274.0. found 274.0.

Step 3. 4-(Imidazo[1,2-b]pyridazin-3-yl)-5-methylthiophene-2-carboxylic acid

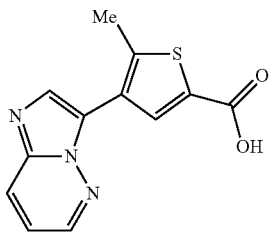 [SMILES: Cc1sc(C(=O)O)cc1-c1cnc2cccnn12]

Methyl 4-(imidazo[1,2-b]pyridazin-3-yl)-5-methylthiophene-2-carboxylate (0.54 g, 1.98 mmol) was dissolved in methanol (9.88 mL) and THF (9.88 mL) and a solution of KOH in methanol was added (1 M, 5.93 mL, 5.93 mmol). The reaction mixture was left to stir overnight at 60° C. The reaction mixture was then cooled to room temperature, concentrated, and acidified with aqueous 1N HCl. The aqueous layer was extracted three times with ethyl acetate, then extracted one time with a 3:1 CHCl$_3$:isopropanol mixture. The combined organics were dried with magnesium sulfate, filtered, and concentrated to afford the title compound. $^1$H NMR (500 MHz, CD$_3$SOCD$_3$) δ 8.77 (d, 1H); 8.34 (d, 1H); 8.25 (s, 1H); 8.11 (s, 1H); 7.51 (dd, 1H); 2.56 (s, 3H). LRMS (APCI) calc'd for (C$_{12}$H$_9$N$_3$O$_2$S) [M+H]$^+$, 260.0. found 260.0.

Step 4. N-[(1R,6R)-6-Amino-2,2-difluorocyclohexyl]-4-(imidazo[1,2-b]pyridazin-3-yl)-5-methylthiophene-2-carboxamide

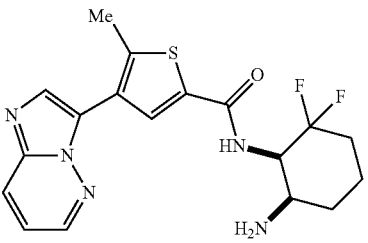

To a mixture of 4-(imidazo[1,2-b]pyridazin-3-yl)-5-methylthiophene-2-carboxylic acid (0.06 g, 0.24 mmol) and BOP (0.16 g, 0.36 mmol) was added tert-butyl[(1R,2R)-2-amino-3,3-difluorocyclohexyl]carbamate (0.06 g, 0.26 mmol) followed by diisopropylethylamine (0.09 mL, 0.49 mmol). The mixture was allowed stir at room temperature overnight. The resulting solution was diluted with water and extracted three times with dichloromethane. The combined organic layers were dried with magnesium sulfate, filtered, concentrated and to the resulting residue was added dichloromethane and trifluoroacetic acid (1 mL, 53 mmol). The compound was purified by prep HPLC. The compound was neutralized by taking the fractions and adding an aqueous saturated sodium bicarbonate solution and extracting three times with ethyl acetate. The combined organics were dried with magnesium sulfate, filtered, and concentrated to afford the title compound as a yellow solid. $^1$H NMR (500 MHz, CD$_3$SOCD$_3$) δ 8.62 (d, 1H); 8.28 (s, 1H); 8.21 (d, 1H); 7.99 (s, 1H); 7.90 (d, 1H); 7.29 (dd, 1H); 4.55 (m, 1H); 3.08 (m, 1H); 2.47 (s, 3H); 2.11 (m, 1H); 1.85 (m, 1H); 1.71 (m, TH); 1.59 (m, 2H); 1.45 (m, 1H). LRMS (APCI) calc'd for (C$_{18}$H$_{19}$F$_2$N$_5$OS) [M+H]$^+$, 392.1. found 392.1.

According to Example 1, the following compounds were prepared from the corresponding 3-bromoimidazo[1,2-b]pyridazine or 3-bromoimidazo[1,2-a]pyridine, thiophene boronic ester, and amine.

| Ex. | Structure | Name | MS |
|---|---|---|---|
| 2 | 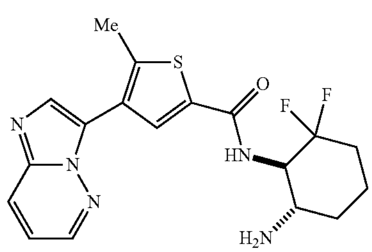 | N-[(1R,6S)-6-amino-2,2-difluorocyclohexyl]-4-(imidazo[1,2-b]pyridazin-3-yl)-5-methylthiophene-2-carboxamide | calc'd (M + H)$^+$ 392.1; found (M + H)$^+$ 392.1 |

-continued

| Ex. | Structure | Name | MS |
|---|---|---|---|
| 3 | 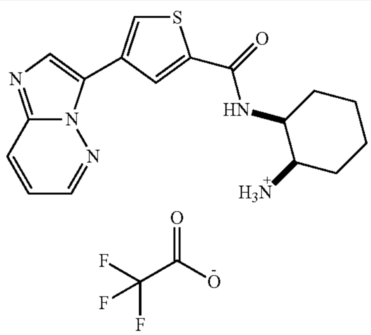 | cis-2-({[4-(imidazo[1,2-b]pyridazin-3-yl)thiophen-2-yl]carbonyl}amino)cyclohex-anaminium trifluoroacetate | calc'd (M + H)+ 342.1; found (M + H)+ 342.1 |
| 4 | 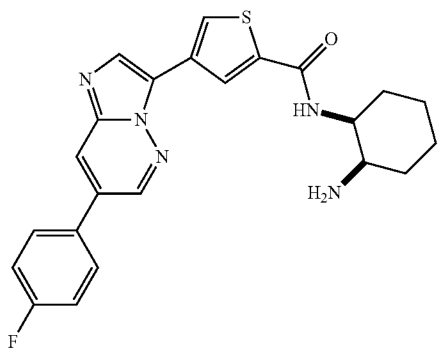 | N-[cis-2-aminocyclohexyl]-4-[7-(4-fluorophenyl)imidazo[1,2-b]pyridazin-3-yl]thiophene-2-carboxamide | calc'd (M + H)+ 436.2; found (M + H)+ 436.1 |
| 5 | 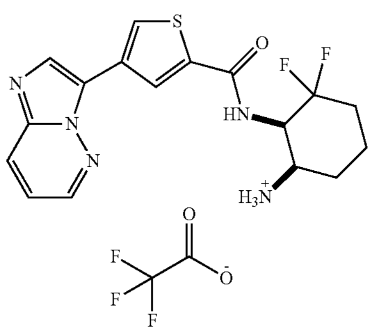 | (1R,2R)-3,3-difluoro-2-({[4-(imidazo[1,2-b]pyridazin-3-yl)thiophen-2-yl]carbonyl}amino)cyclohex-anaminium trifluoroacetate | calc'd (M + H)+ 378.1; found (M + H)+ 378.1 |
| 6 | 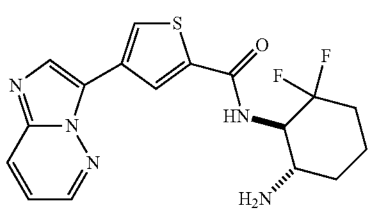 | N-[(1R,6S)-6-amino-2,2-difluorocyclohexyl]-4-(imidazo[1,2-b]pyridazin-3-yl)thiophene-2-carboxamide | calc'd (M + H)+ 378.1; found (M + H)+ 378.1 |
| 7 | 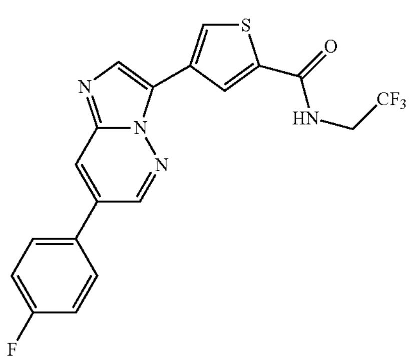 [SMILES: O=C(NCC(F)(F)F)c1cc(-c2cnc3cc(-c4ccc(F)cc4)cnn23)cs1] | 4-[7-(4-fluorophenyl)imidazo[1,2-b]pyridazin-3-yl]-N-(2,2,2-trifluoroethyl)thiophene-2-carboxamide | calc'd (M + H)+ 421.1; found (M + H)+ 421.0 |

-continued

| Ex. | Structure | Name | MS |
|---|---|---|---|
| 8 | 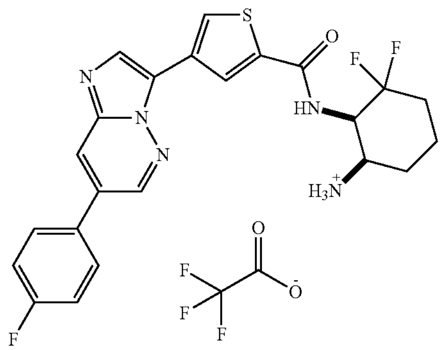 | (1R,2R)-3,3-difluoro-2-[({4-[7-(4-fluorophenyl)imidazo[1,2-b]pyridazin-3-yl]thiophen-2-yl}carbonyl)amino]cyclohexanaminium trifluoroacetate | calc'd (M + H)$^+$ 472.1; found (M + H)$^+$ 472.1 |
| 9 | 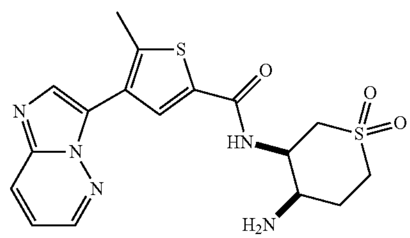 | N-[(cis-4-amino-1,1-dioxidotetrahydro-2H-thiopyran-3-yl]-4-(imidazo[1,2-b]pyridazin-3-yl)-5-methylthiophene-2-carboxamide | calcd'd (M + H)$^+$ 406.1; found (M + H)$^+$ 406.1 |
| 10 | 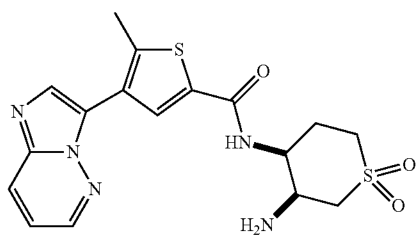 | N-[cis-3-amino-1,1-dioxidotetrahydro-2H-thiopyran-4-yl]-4-(imidazo[1,2-b]pyridazin-3-yl)-5-methylthiophene-2-carboxamide | calc'd (M + H)$^+$ 406.1; found (M + H)$^+$ 406.1 |
| 11 | 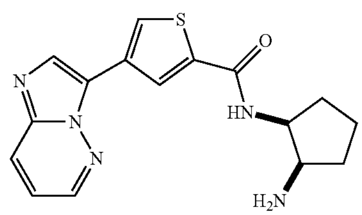 | N-[cis-2-aminocyclopentyl]-4-(imidazo[1,2-b]pyridazin-3-yl)thiophene-2-carboxamide | calc'd (M + H)$^+$ 328.1; found (M + H)$^+$ 328.0 |
| 12 | 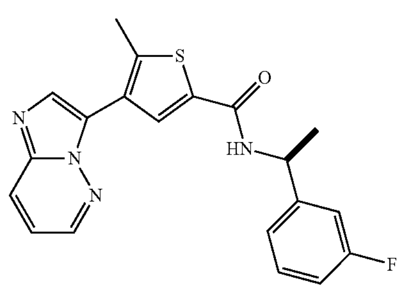 [SMILES: Cc1sc(C(=O)N[C@@H](C)c2cccc(F)c2)cc1-c1cnc2cccnn12] | N-[(1S)-1-(3-fluorophenyl)ethyl]-4-(imidazo[1,2-b]pyridazin-3-yl)-5-methylthiophene-2-carboxamide | calcd'd (M + H)$^+$ 381.1; found (M + H)$^+$ 381.1 |
| 13 | 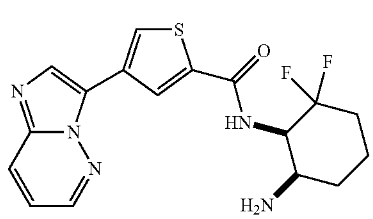 | N-[(1R,6R)-6-amino-2,2-difluorocyclohexyl]-4-(imidazo[1,2-a]pyridin-3-yl)thiophene-2-carboxamide | calc'd (M + H)$^+$ 377.1; found (M + H)$^+$ 377.1 |

| Ex. | Structure | Name | MS |
|---|---|---|---|
| 14 | 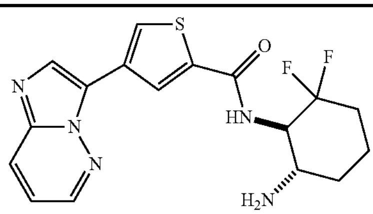 | N-[(1R,6S)-6-amino-2,2-difluorocyclohexyl]-4-(imidazo[1,2-a]pyridin-3-yl)thiophene-2-carboxamide | calc'd (M + H)+ 377.1; found (M + H)+ 377.1 |
| 15 | 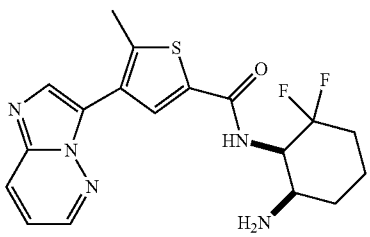 | N-[(1R,6R)-6-amino-2,2-difluorocyclohexyl]-4-(imidazo[1,2-a]pyridin-3-yl)-5-methylthiophene-2-carboxamide | calc'd (M + H)+ 391.1; found (M + H)+ 391.1 |
| 16 | 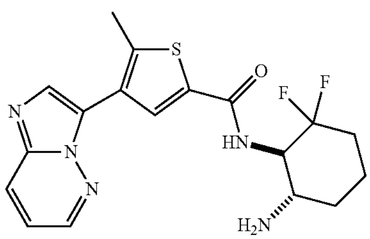 | N-[(1R,6S)-6-amino-2,2-difluorocyclohexyl]-4-(imidazo[1,2-a]pyridin-3-yl)-5-methylthiophene-2-carboxamide | calc'd (M + H)+ 391.1; found (M + H)+ 391.1 |
| 17 | 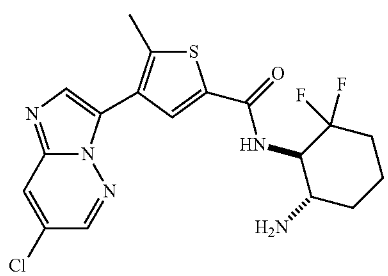 | N-[(1R,6S)-6-amino-2,2-difluorocyclohexyl]-4-(7-chloroimidazo[1,2-a]pyridin-3-yl)-5-methylthiophene-2-carboxamide | calcd'd (M + H)+ 425.1; found (M + H)+ 425.0 |

Example 18

N-[(1R,6R)-6-Amino-2,2-difluorocyclohexyl]-5-ethyl-4-(imidazo[1,2-b]pyridazin-3-yl)thiophene-2-carboxamide

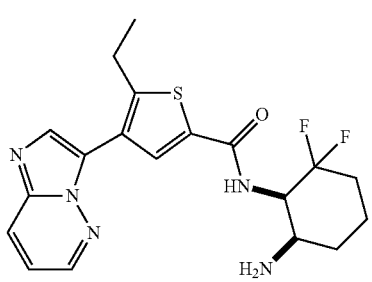

Step 1. Methyl 4-(imidazo[1,2-b]pyridazin-3-yl)thiophene-2-carboxylate

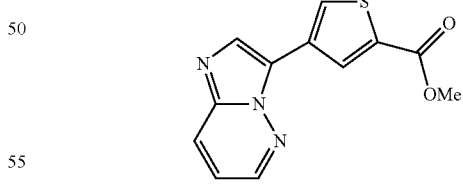

3-Bromoimidazo[1,2-b]pyridazine (700 mg, 3.53 mmol), methyl 5-methyl-4-(4,4,5,5-tetramethyl-1,3,2-dioxaborolan-2-yl)thiophene-2-carboxylate (1.04 g, 3.89 mmol), Pd$_2$(dba)$_3$ (324 mg, 0.353 mmol), tricyclohexylphosphine (248 mg, 0.884 mmol), aqueous tribasic potassium phosphate (2.54 mL, 12.0 mmol, 1.27 M), and 1,4-dioxane (17.7 mL) were placed in a sealed tube and purged with nitrogen for 5 minutes. The solution was heated to 100° C. for 1.5 h, after which the reaction was cooled to room temperature. Saturated aqueous sodium bicarbonate was added to the mixture. The aqueous layer was then extracted with ethyl acetate (×3). The combined organic layers were then dried with magnesium sulfate, filtered, and concentrated under reduced pressure. The residue was purified by flash chromatography affording the title compound as a yellow solid. $^1$H NMR (500 MHz, CD$_3$SOCD$_3$) δ 8.70 (d, 1H); 8.68 (s, 1H); 8.54 (s, 1H); 8.42 (s, 1H); 8.22 (d, 1H); 7.31 (dd, 1H); 3.86 (s, 3H). LRMS (APCI) calc'd for (C$_{12}$H$_9$N$_3$O$_2$S) [M+H]$^+$, 260.0. found 260.0.

Step 2. Methyl 5-bromo-4-(imidazo[1,2-b]pyridazin-3-yl)thiophene-2-carboxylate

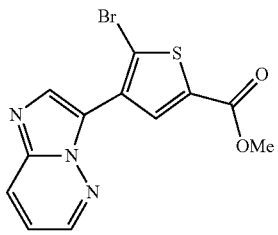 [SMILES: COC(=O)c1cc(-c2cnc3cccnn23)c(Br)s1]

Methyl 4-(imidazo[1,2-b]pyridazin-3-yl)thiophene-2-carboxylate (690 mg, 2.66 mmol) was dissolved in thionyl bromide (5 mL, 64.5 mmol) and heated at 50° C. in a sealed tube for 4 h. The solution poured over ice and quenched with ammonium hydroxide. The aqueous layer was extracted with dichloromethane (×3). The organic layers put together, dried with magnesium sulfate, filtered, and concentrated under reduced pressure. The residue was purified by flash chromatography to afford the title compound as a light brown solid. $^1$H NMR (500 MHz, CD$_3$SOCD$_3$) δ 8.66 (d, 1H); 8.27 (s, 1H); 8.25 (s, 1H); 8.25 (d, 1H); 7.35 (dd, 1H); 3.85 (s, 3H). LRMS (APCI) calc'd for (C$_{12}$H$_8$BrN$_3$O$_2$S) [M+H]$^+$, 338.0. found 337.9.

Step 3. Methyl 5-ethenyl-4-(imidazo[1,2-b]pyridazin-3-yl)thiophene-2-carboxylate

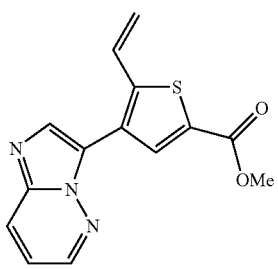 [SMILES: C=Cc1sc(C(=O)OC)cc1-c1cnc2cccnn12]

Methyl-5-bromo-4-(imidazo[1,2-b]pyridazin-3-yl)thiophene-2-carboxylate (200 mg, 0.591 mmol), potassium vinyltrifluoroborate (119 mg, 0.887 mmol), PdCl$_2$(dppf)-CH$_2$Cl$_2$ adduct (48 mg, 0.059 mmol), and triethylamine (0.165 mL, 1.18 mmol) was dissolved in n-propanol (5.91 mL) and purged with nitrogen for 5 minutes in a sealed tube. The solution was heated at 100° C. for 18 h. the reaction was cooled to room temperature and quenched with saturated sodium bicarbonate. The aqueous layer was extracted with ethyl acetate (×3) and the organic layers combined, dried with magnesium sulfate, filtered, and concentrated under reduced pressure. The residue was purified by flash chromatography to afford the title compound as an orange solid. $^1$H NMR (500 MHz, CD$_3$SOCD$_3$) δ 8.61 (d, 1H); 8.23 (d, 1H); 8.16 (s, 1H); 7.95 (s, 1H); 7.32 (dd, 1H); 6.94 (dd, 1H); 5.87 (d, 1H); 5.44 (d, 1H); 3.85 (s, 3H). LRMS (APCI) calc'd for (C$_{14}$H$_{11}$N$_3$O$_2$S) [M+11]$^+$, 286.1. found 286.0.

Step 4. 5-Ethenyl-4-(imidazo[1,2-b]pyridazin-3-yl)thiophene-2-carboxylic acid

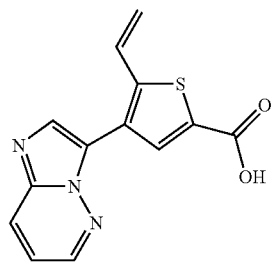 [SMILES: C=Cc1sc(C(=O)O)cc1-c1cnc2cccnn12]

Methyl 5-ethenyl-4-(imidazo[1,2-b]pyridazin-3-yl)thiophene-2-carboxylate (130 mg, 0.456 mmol) was dissolved in methanol (2.28 mL) and THF (2.28 mL) and 1M KOH in MeOH (1.38 mL, 1.38 mmol) was added to the mixture. The solution was left to stir at 60° C. for 18 h. The reaction was cooled to room temperature and concentrated under reduced pressure. 1N HCl was added to the residue and the precipitate filtered. The precipitate was then dried under high vacuum affording the title compound as a yellow solid. $^1$H NMR (500 MHz, CD$_3$SOCD$_3$) δ 13.37 (s, 1H, br); 8.62 (d, 1H); 8.23 (d, 1H); 8.07 (s, 1H); 7.96 (s, 1H); 7.33 (dd, 1H); 6.91 (dd, 1H); 5.84 (d, 1H); 5.41 (d, 1H). LRMS (APCI) calc'd for (C$_{13}$H$_9$N$_3$O$_2$S) [M+H]$^+$, 272.0. found 272.0.

Step 5. tert-Butyl[(1R,2R)-2-({[5-ethenyl-4-(imidazo[1,2-b]pyridazin-3-yl)thiophen-2-yl]carbonyl}amino)-3,3-difluorocyclohexyl]carbamate

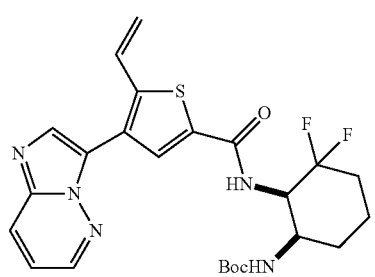

To a mixture of 5-(ethenyl-4-(imidazo[1,2-b]pyridazin-3-yl)thiophene-2-carboxylic acid (105 mg, 0.387 mmol) and BOP (257 mg, 0.581 mmol) in DMF (5.2 mL) was added tert-butyl [(1R,2R)-2-amino-3,3-difluorocyclohexyl]carbamate (145 mg, 0.581 mmol) followed by diisopropylethyl amine (0.169 mL, 0.968 mmol). The mixture was allowed to stir at room temperature for 18 h. After the reaction was complete, water was added and the aqueous layer extracted with ethyl acetate (×3). The organic layers were combined, dried with magnesium sulfate, filtered, and concentrated under reduced pressure. The residue was purified by flash chromatography giving the title compound as an orange solid. LRMS (APCI) calc'd for ($C_{24}H_{27}F_2N_5O_3S$) [M+H]$^+$, 504.2. found 504.1.

Step 6. N-[(1R,6R)-6-Amino-2,2-difluorocyclohexyl]-5-ethyl-4-(imidazo[1,2-b]pyridazin-3-yl)thiophene-2-carboxamide

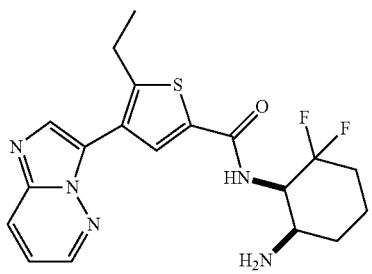

tert-Butyl[(1R,2R)-2-({[5-ethenyl-4-(imidazo[1,2-b]pyridazin-3-yl)thiophen-2-yl]carbonyl}amino)-3,3-difluorocyclohexyl]carbamate (103 mg, 0.205 mmol), ammonium formate (128 mg, 2.04 mmol), and 10% Pd/C (109 mg, 0.102 mmol) were dissolved in n-propanol (4.1 mL) and left to stir at 100° C. for 18 h. The solution was cooled to room temperature and filtered through celite. The filtrate was concentrated under reduced pressure and taken up in dichloromethane (2 mL). Trifluoroacetic acid (1 mL, 13.0 mmol) was added to the mixture and stirred for 4 h at room temperature. The solution was then neutralized with aqueous saturated sodium bicarbonate and extracted with dichloromethane (×3). The organic layers were collected and dried with magnesium sulfate, filtered, and concentrated under reduced pressure. The residue was then purified by prep HPLC. The compound was neutralized by taking the fractions and adding an aqueous saturated sodium bicarbonate solution and extracting three times with dichloromethane. The combined organics were dried with magnesium sulfate, filtered, and concentrated to afford the title compound as a yellow solid. $^1$H NMR (500 MHz, CD$_3$SOCD$_3$) δ 8.60 (d, 1H); 8.22 (s, 1H); 8.21 (d, 1H); 7.95 (s, 1H); 7.90 (d, 114, br); 7.29 (dd, 1H); 4.56 (m, 1H); 3.08 (m, 1H); 2.83 (q, 2H); 2.10 (m, 1H); 1.86 (m, 1H); 1.71 (m, 1H); 1.59 (m, 2H); 1.44 (m, 1H); 1.20 (t, 3H). LRMS (APCI) calc'd for ($C_{19}H_{21}F_2N_5OS$) [M+H]$^+$, 406.1. found 406.1.

According to Example 18, the following compounds were prepared from the corresponding 3-bromoimidazo[1,2-b]pyridazine or 3-bromoimidazo[1,2-a]pyridine, borate salt or boronic ester, and amine.

| Ex. | Structure | Name | MS |
|---|---|---|---|
| 19 | 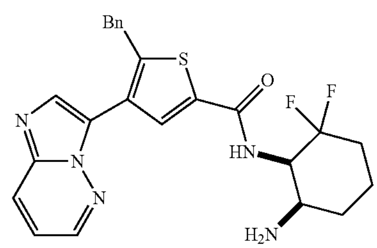 | N-[(1R,6R)-6-amino-2,2-difluorocyclohexyl]-5-benzyl-4-(imidazo[1,2-b]pyridazin-3-yl)thiophene-2-carboxamide | calc'd (M + H)$^+$ 468.2; found (M + H)$^+$ 468.1 |
| 20 | 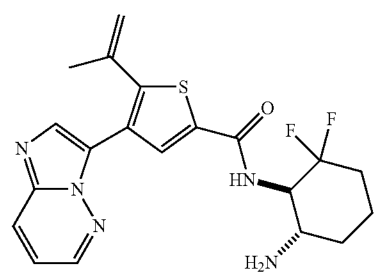 | N-[(1R,6S)-6-amino-2,2-difluorocyclohexyl]-4-(imidazo[1,2-b]pyridazin-3-yl)-5-(prop-1-en-2-yl)thiophene-2-carboxamide | calc'd (M + H)$^+$ 418.1; found (M + H)$^+$ 418.1 |
| 21 | 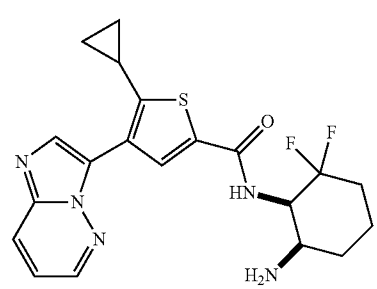 | N-[(1R,6R)-6-amino-2,2-difluorocyclohexyl]-5-cyclopropyl-4-(imidazo[1,2-b]pyridazin-3-yl)thiophene-2-carboxamide | calc'd (M + H)$^+$ 418.1; found (M + H)$^+$ 418.1 |

| Ex. | Structure | Name | MS |
|---|---|---|---|
| 22 | 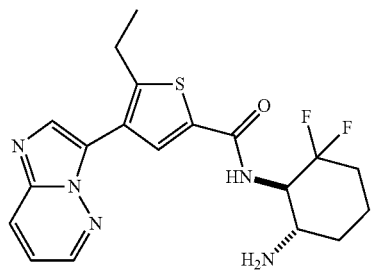 | N-[(1R,6R)-6-amino-2,2-difluorocyclohexyl]-5-ethyl-4-(imidazo[1,2-a]pyridin-3-yl)thiophene-2-carboxamide | calc'd (M + H)⁺ 405.1; found (M + H)⁺ 405.1 |

Example 23

N-[(1R,6S)-6-Amino-2,2-difluorocyclohexyl]-5-ethyl-4-(imidazo[1,2-b]pyridazin-3-yl)thiophene-2-carboxamide

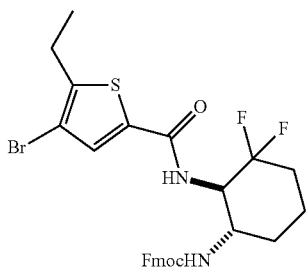

Step 1. 9H-Fluoren-9-ylmethyl[(1S,2R)-2-{[(4-bromo-5-ethylthiophen-2-yl)carbonyl]amino}-3,3-difluorocyclohexyl]carbamate

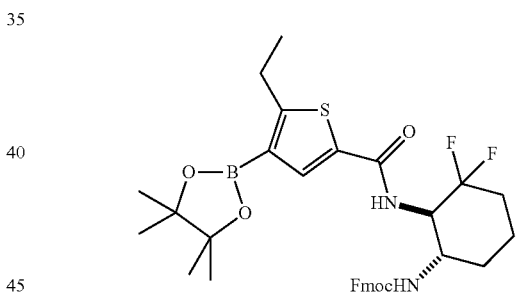

4-Bromo-5-ethylthiophene-2-carboxylic acid (300 mg, 1.15 mmol) and BOP (762 mg, 1.72 mmol) were dissolved in DMF (11.5 mL) and stirred at room temperature for 5 minutes. (1R,6S)-6-{[(9H-fluoren-9-ylmethoxy)carbonyl]amino}-2,2-difluorocyclohexanaminium chloride (432 mg, 1.16 mmol) was added followed by diisopropylethyl amine (0.50 mL, 2.87 mmol) and the solution was stirred at room temperature for 18 h. The solution was diluted with water, and extracted with dichloromethane (×3). The organic layers were collected, dried with magnesium sulfate, filtered, and concentrated under reduced pressure. The residue was purified by flash chromatography affording the title compound as an orange oil. ¹H NMR (500 MHz, CDCl₃) δ 7.72 (d, 2H); 7.46 (dd, 2H); 7.36 (s, 1H); 7.35 (d, 2H); 7.23 (dd, 2H); 6.36 (d, 1H); 5.14 (d, 1H); 4.36 (dd, 1H); 4.29 (dd, 1H); 4.13 (dd, 1H); 4.01 (dd, 1H); 3.86 (dd, 1H); 2.70 (q, 2H); 2.82 (m, 1H); 2.17 (m, 1H); 1.86 (m, 2H); 1.65 (m, 1H); 1.43 (m, 1H); 1.18 (t, 3H). LRMS (APCI) calc'd for ($C_{28}H_{27}BrF_2N_2O_3S$) [M+H]⁺, 589.1. found 589.1.

Step 2. 9H-Fluoren-9-ylmethyl[(1S,2R)-2-({[5-ethyl-4-(4,4,5,5-tetramethyl-1,3,2-dioxaborolan-2-yl)thiophen-2-yl]carbonyl}amino)-3,3-difluorocyclohexyl]carbamate 9H-Fluoren-9-ylmethyl[(1S,2R)-2-{[(4-bromo-5-ethylthiophen-2-yl)carbonyl]amino}-3,3-difluorocyclohexyl]carbamate (677 mg, 1.15 mmol), bis(pinacolato)diboron (321 mg, 1.26 mmol), PdCl₂(dppf)-CH₂Cl₂ adduct (56 mg, 0.07 mmol), dppf (38 mg, 0.07 mmol), and potassium acetate (451 mg, 4.59 mmol) were placed into a sealed tube and 1,4-dioxane added (11.5 mL) and the tube purged with nitrogen for 15 minutes. The solution was heated at 85° C. for 18 h. The solution was cooled to room temperature and additional bis(pinacolato)diboron (146 mg, 0.58 mmol), PdCl₂(dppf)-CH₂Cl₂ adduct (56 mg, 0.07 mmol), dppf (38 mg, 0.07 mmol), and potassium acetate (225 mg, 2.3 mmol) were added. The solution was purged with nitrogen for 15 minutes and heated at 85° C. for 18 h. The solution was cooled to room temperature, diluted with water, and extracted with dichloromethane (×3). The organic layers were collected, dried with magnesium sulfate, filtered, and concentrated under reduced pressure. The residue was purified by column chromatography affording the title compound as an orange solid. LRMS (APCI) calc'd for ($C_{34}H_{39}BF_2N_2O_5S$) [M+H]$^+$, 637.3. found 637.3.

Step 3. 9H-Fluoren-9-ylmethyl[(1S,2R)-2-({[5-ethyl-4-(imidazo[1,2-b]pyridazin-3-yl)thiophen-2-yl]carbonyl}amino)-3,3-difluorocyclohexyl]carbamate

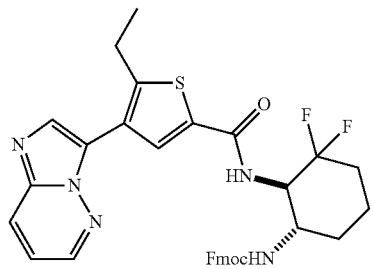

3-Bromoimidazo[1,2-b]pyridazine (53 mg, 0.27 mmol), 9H-fluoren-9-ylmethyl[(1S,2R)-2-({[5-ethyl-4-(4,4,5,5-tetramethyl-1,3,2-dioxaborolan-2-yl)thiophen-2-yl]carbonyl}amino)-3,3-difluorocyclohexyl]carbamate (187 mg, 0.294 mmol), Pd$_2$(dba)$_3$ (25 mg, 0.03 mmol), tricyclohexylphosphine (19 mg, 0.07 mmol), and aqueous tribasic potassium acetate (0.71 mL, 0.91 mmol, 1.27 M) were placed into a sealed tube and 1,4-dioxane (5.4 mL) added. The sealed tube was purged with nitrogen for 5 minutes and heated at 100° C. for 18 h. The solution was cooled to room temperature and additional 9H-fluoren-9-ylmethyl[(1S,2R)-2-({[5-ethyl-4-(4,4,5,5-tetramethyl-1,3,2-dioxaborolan-2-yl)thiophen-2-yl]carbonyl}amino)-3,3-difluorocyclohexyl]carbamate (85 mg, 0.13 mmol), Pd$_2$(dba)$_3$ (12 mg, 0.01 mmol), tricyclohexylphosphine (8 mg, 0.03 mmol), and aqueous tribasic potassium acetate (0.42 mL, 0.54 mmol, 1.27 M) were added. The sealed tube was purged with nitrogen for 5 minutes and heat at 100° C. for 4 h. The solution was then cooled to room temperature and quenched with aqueous saturated sodium bicarbonate and extracted with dichloromethane (×3). The combined organic layers were dried with magnesium sulfate, filtered, and concentrated under reduced pressure. The residue was taken on to the deprotection step without purification. LRMS (APCI) calc'd for ($C_{34}H_{31}F_2N_5O_3S$) [M+H]$^+$, 628.2. found 628.2.

Step 4. N-[(1R,6S)-6-Amino-2,2-difluorocyclohexyl]-5-ethyl-4-(imidazo[1,2-b]pyridazin-3-yl)thiophene-2-carboxamide

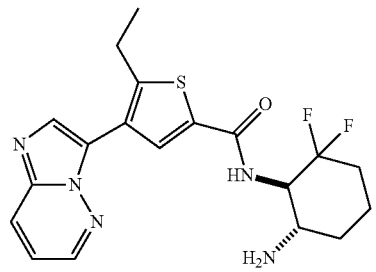

9H-Fluoren-9-ylmethyl[(1S,2R)-2-({[5-ethyl-4-(imidazo[1,2-b]pyridazin-3-yl)thiophen-2-yl]carbonyl}amino)-3,3-difluorocyclohexyl]carbamate (168 mg, 0.268 mmol) was dissolved in DMF (2.68 mL) and piperidine added (0.265 mL, 2.68 mmol). The solution was stirred at room temperature for 2 h. The solution was then subjected to prep HPLC for purification. The compound was neutralized by taking the fractions and adding an aqueous saturated sodium bicarbonate solution and extracting three times with dichloromethane. The combined organics were dried with magnesium sulfate, filtered, and concentrated to afford the title compound as a yellow solid. $^1$H NMR (500 MHz, CD$_3$SOCD$_3$) δ 8.61 (d, 1H); 8.41 (d, 1H); 8.21 (d, 1H); 8.19 (s, 1H); 7.95 (s, 1H); 7.29 (dd, 1H); 4.07 (m, 1H); 2.86 (m, 1H); 2.85 (q, 2H); 2.07 (m, 1H); 1.88 (m, 1H); 1.86 (m, 1H); 1.70 (m, 1H); 1.36 (m, 2H); 1.21 (t, 3H). LRMS (APCI) calc'd for ($C_{19}H_{21}F_2N_5OS$) [MA-1]$^+$, 406.1. found 406.1.

According to Example 23, the following compounds were prepared from the corresponding 3-bromoimidazo[1,2-b]pyridazine and amine.

| Ex. | Structure | Name | MS |
| --- | --- | --- | --- |
| 24 | ![structure] | N-[(1R,6R)-6-amino-2,2-difluorocyclohexyl]-5-ethyl-4-[7-(trifluoromethyl)imidazo[1,2-b]pyridazin-3-yl]thiophene-2-carboxamide | calc'd (M + H)$^+$ 474.1; found (M + H)$^+$ 474.1 |

| Ex. | Structure | Name | MS |
|---|---|---|---|
| 25 | 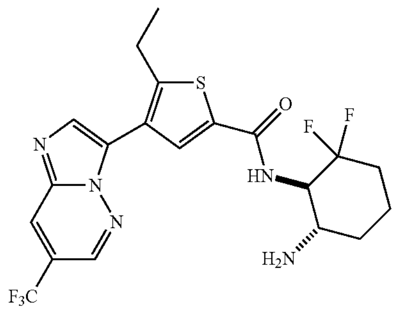 | N-[(1R,6S)-6-amino-2,2-difluorocyclohexyl]-5-ethyl-4-[7-(trifluoromethyl)imidazo[1,2-b]pyridazin-3-yl]thiophene-2-carboxamide | calc'd (M + H)⁺ 474.1; found (M + H)⁺ 474.1 |

Example 26

N-[(1R,6S)-6-Amino-2,2-difluorocyclohexyl]-5-(difluoromethyl)-4-(imidazo[1,2-b]pyridazin-3-yl)thiophene-2-carboxamide

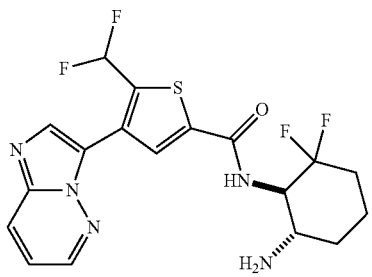

Step 1. Methyl 5-formyl-4-(imidazo[1,2-b]pyridazin-3-yl)thiophene-2-carboxylate

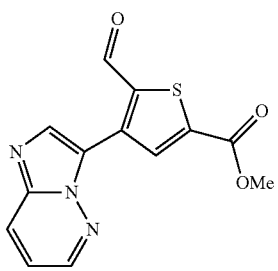 [SMILES: COC(=O)c1cc(-c2cnc3cccnn23)c(C=O)s1]

To a stirred solution of methyl 5-ethenyl-4-(imidazo[1,2-b]pyridazin-3-yl)thiophene-2-carboxylate (160 mg, 0.56 mmol) in THF (1.9 mL) and water (0.95 mL) were added OsO₄ (4% in water, 0.36 mL, 0.056 mmol) and NMO (79 mg, 0.67 mmol). The reaction mixture was left to stir for 5 h, treated with additional 0504 (4% in water, 0.36 mL, 0.056 mmol) and NMO (79 mg, 0.67 mmol), and left to stir overnight. Additional OsO₄ (4% in water, 0.36 mL, 0.056 mmol) and NMO (79 mg, 0.67 mmol) were added and the resultant solution was left to stir for 1 d, treated with aqueous sodium thiosulfate, and left to stir for 2 h. The mixture was extracted with dichloromethane (×3). The combined organics were dried (sodium sulfate), and concentrated. The residue was dissolved in THF (6 mL) and water (3 mL), and treated with sodium periodate (143 mg, 0.67 mmol). The mixture was left to stir overnight, diluted with water, and extracted with dichloromethane (×3). The combined organics were dried (sodium sulfate), concentrated, and purified by flash chromatography to afford the title compound as a yellow solid. LRMS (APCI) calc'd for ($C_{13}H_{10}N_3O_3S$) [M+H]⁺, 288.0. found 288.0.

Step 2. Methyl 5-(difluoromethyl)-4-(imidazo[1,2-b]pyridazin-3-yl)thiophene-2-carboxylate

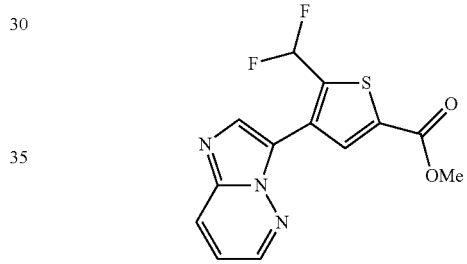

To a stirred solution of methyl 5-formyl-4-(imidazo[1,2-b]pyridazin-3-yl)thiophene-2-carboxylate (80 mg, 0.28 mmol) in dichloromethane (5.6 mL) was added Deoxo-Fluor (50%, 616 mg, 1.39 mmol). The reaction mixture was left to stir overnight, treated with aqueous sodium bicarbonate solution, and extracted with dichloromethane (×3). The combined organics were washed with brine, dried (sodium sulfate), concentrated, and purified by flash chromatography to afford the title compound. ¹H NMR (500 MHz, CD₃SOCD₃) δ 8.66 (dd, 1H); 8.32 (t, 1H); 8.26 (dd, 1H); 8.01 (s, 1H); 7.45 (t, 1H); 7.37 (dd, 1H); 3.89 (s, 3H). LRMS (APCI) calc'd for ($C_{13}H_{10}F_2N_3O_2S$) [M+H]⁺, 310.0. found 310.0.

Step 3. 5-(Difluoromethyl)-4-(imidazo[1,2-b]pyridazin-3-yl)thiophene-2-carboxylic acid

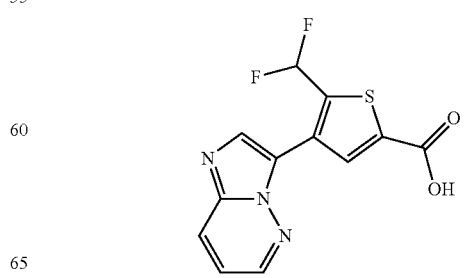

To a stirred solution of methyl 5-(difluoromethyl)-4-(imidazo[1,2-b]pyridazin-3-yl)thiophene-2-carboxylate (57 mg, 0.18 mmol) in methanol (1 mL) and water (0.5 mL) was added NaOH (2 N, 0.28 mL, 0.56 mmol). The mixture was heated to 50° C. for 1 h, cooled to room temperature, and acidified with 1 N HCl. The resultant mixture was concentrated, and used in the next step without further purification. LRMS (APCI) calc'd for $(C_{12}H_8F_2N_3O_2S)$ $[M+H]^+$, 296.0. found 296.0.

Step 4. N-[(1R,6S)-6-Amino-2,2-difluorocyclohexyl]-5-(difluoromethyl)-4-(imidazo[1,2-b]pyridazin-3-yl)thiophene-2-carboxamide

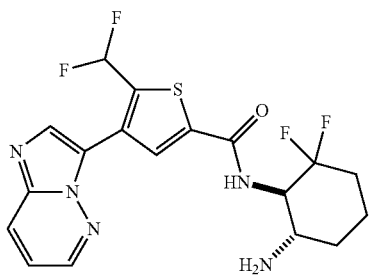

To 5-(difluoromethyl)-4-(imidazo[1,2-b]pyridazin-3-yl)thiophene-2-carboxylic acid (26 mg, 0.088 mmol) in DMF (0.4 mL) were added BOP (58 mg, 0.13 mmol) and DIEA (0.062 mL, 0.35 mmol). The mixture was left to stir for 5 min, treated with (1R,6S)-6-{[(9H-fluoren-9-ylmethoxy)carbonyl]amino}-2,2-difluorocyclohexanaminium chloride (36 mg, 0.088 mmol), and left to stir for 2 h. The mixture was diluted with water and extracted with EtOAc (×3). The combined organics were dried (sodium sulfate), concentrated, and purified by flash chromatography to afford 9H-fluoren-9-ylmethyl[(1S,2R)-2-({[5-(difluoromethyl)-4-(imidazo[1,2-b]pyridazin-3-yl)thiophen-2-yl]carbonyl}amino)-3,3-difluorocyclohexyl]carbamate. LRMS (APCI) calc'd for $(C_{33}H_{28}F_4N_5O_3S)$ $[M+H]^+$, 650.2. found 650.2.

To a stirred solution of 9H-fluoren-9-ylmethyl[(1S,2R)-2-({[5-(difluoromethyl)-4-(imidazo[1,2-b]pyridazin-3-yl)thiophen-2-yl]carbonyl}amino)-3,3-difluorocyclohexyl]carbamate (27 mg, 0.042 mmol) in DMF (0.8 mL) was added piperidine (0.08 mL, 0.83 mmol). The mixture was left to stir for 1 h, diluted with water, and extracted with EtOAc. The organic layer was dried, concentrated, and purified by flash chromatography to afford the title compound. $^1$H NMR (500 MHz, CD$_3$SOCD$_3$) δ 8.38 (s, 1H); 8.72 (d, 1H); 8.68 (dd, 1H); 8.43 (s, 1H); 8.27 (dd, 1H); 7.97 (s, 1H); 7.38 (dd, 1H); 7.35 (t, 1H); 4.05 (m, 1H); 2.82 (m, 1H); 1.30-2.10 (m, 6H). LRMS (APCI) calc'd for $(C_{18}H_{18}F_4N_5OS)$ $[M+H]^+$, 428.1. found 428.1.

According to Example 26, Example 27 was prepared from the corresponding amine.

Example 27

N-[(1R,6R)-6-Amino-2,2-difluorocyclohexyl]-5-(difluoromethyl)-4-(imidazo[1,2-b]pyridazin-3-yl)thiophene-2-carboxamide

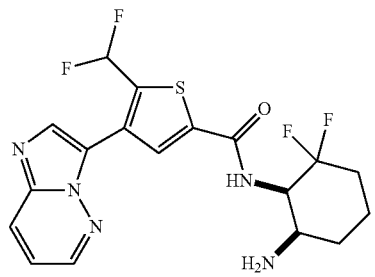

calc'd. $(M+H)^+$ 428.1. found $(M+H)^+$ 428.1

Example 28

N-[(1R,6S)-6-Amino-2,2-difluorocyclohexyl]-5-chloro-4-(imidazo[1,2-b]pyridazin-3-yl)-1,3-thiazole-2-carboxamide

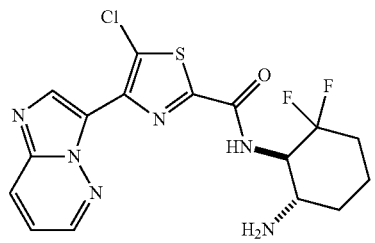

Step 1. 1-(Imidazo[1,2-b]pyridazin-3-yl)ethanone

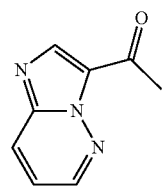

3-Bromoimidazo[1,2-b]pyridazine (1.0 g, 5.05 mmol), tributyl(1-ethoxyvinyl)tin (3.41 mL, 10.1 mmol), and PdCl$_2$(PPh$_3$)$_2$ (354 mg, 0.505 mmol), were added to a sealed tube. DMF (25.2 mL) was added and the reaction purged with nitrogen for 5 minutes. The reaction was heated at 100° C. for 18 h. The reaction was cooled to room temperature and quenched with aqueous saturated sodium bicarbonate. The aqueous layer was extracted with ethyl acetate (×3) and the combined organic layers were dried with magnesium sulfate, filtered, and concentrated under reduced pressure. The residue was diluted with methanol (10 mL) and HCl in 1,4- dioxane (1.26 mL, 5.05 mmol, 4M) was added. The solution was stirred at room temperature for 1 h. The reaction was then quenched with aqueous saturated sodium bicarbonate and extracted with ethyl acetate (×3). The combined organic layers were dried with magnesium sulfate, filtered, and concentrated under reduced pressure. The residue was purified by flash chromatography to afford the title compound. $^1$H NMR (500 MHz, CD$_3$SOCD$_3$) δ 8.76 (d, 1H); 8.55 (s, 1H); 8.31 (d, 1H); 8.49 (dd, 1H); 2.64 (s, 3H). LRMS (APCI) calc'd for (C$_8$H$_7$N$_3$O) [M+H]$^+$, 162.1. found 162.1.

Step 2. 2,2-Dibromo-1-(imidazo[1,2-b]pyridazin-3-yl)ethanone

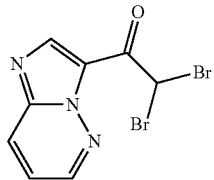 [SMILES: O=C(c1cnc2cccnn12)C(Br)Br]

1-(Imidazo[1,2-b]pyridazin-3-yl)ethanone (502 mg, 3.11 mmol) was dissolved in acetic acid (7.8 mL) and 33% HBr in acetic acid (0.564 mL, 3.11 mmol) was added. Bromine (0.177 mL, 3.43 mmol) was added and the solution stirred at 60° C. for 1.5 h. After stirring for 1.5 h, added more bromine (0.08 mL, 1.56 mmol) and 33% HBr in acetic acid (0.282 mL, 1.56 mmol). The solution was stirred at 60° C. for 3 h. The solution was then cooled to room temperature and quenched with 10% aqueous sodium thiosulfate. The aqueous layer was extracted with dichloromethane (×3). The organic layers were combined and washed with aqueous saturated sodium bicarbonate. The organic layer was collected and dried with magnesium sulfate, filtered, and concentrated under reduced pressure. The residue was taken on to the next step without further purification. $^1$H NMR (500 MHz, CD$_3$SOCD$_3$) δ 8.88 (d, 1H); 8.83 (s, 1H); 8.40 (d, 1H); 7.66 (s, 1H); 7.61 (dd, 1H). LRMS (APCI) calc'd for (C$_8$H$_5$Br$_2$N$_3$O) [M+H]$^+$, 317.9. found 317.9.

Step 3. Ethyl 4-(imidazo[1,2-b]pyridazin-3-yl)-1,3-thiazole-2-carboxylate

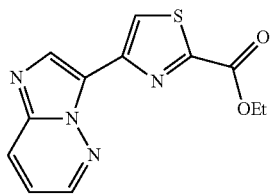 [SMILES: O=C(O)c1nc(-c2cnc3cccnn23)cs1]

2,2-Dibromo-1-(imidazo[1,2-b]pyridazin-3-yl)ethanone (790 mg, 2.48 mmol) and ethyl thiooxamate (547 mg, 3.96 mmol) were dissolved in 1,4-dioxane (24.8 mL) and heated to 100° C. for 4 h. The solution was cooled to room temperature and water was added. The aqueous layer was extracted with ethyl acetate (×3). The organic layers were combined and dried with magnesium sulfate, filtered, and concentrated under reduced pressure to give the title compound as an orange solid. $^1$H NMR (500 MHz, CD$_3$SOCD$_3$) δ 8.79 (s, 1H); 8.77 (d, 1H); 8.33 (s, 1H); 8.30 (d, 1H); 7.39 (dd, 1H); 4.43 (q, 2H); 1.36 (t, 3H). LRMS (APCI) calc'd for (C$_{12}$H$_{10}$N$_4$O$_2$S) [M+H]$^+$, 275.1. found 275.0.

Step 4. 4-(Imidazo[1,2-b]pyridazin-3-yl)-1,3-thiazole-2-carboxylic acid

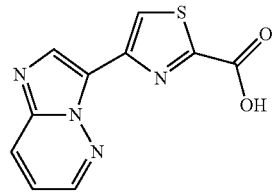

Ethyl 4-(imidazo[1,2-b]pyridazin-3-yl)-1,3-triazole-2-carboxylate (100 mg, 0.365 mmol) was dissolved in methanol (0.91 mL) and THF (0.91 mL) and KOH in methanol (1.09 mL, 1.09 mmol, 1M) was added. The solution was left to stir at 60° C. for 18 h. The reaction was then cooled to room temperature and concentrated under reduced pressure. To the residue was added 1N HCl. The precipitate was filtered and dried under high vacuum to afford the title compound as an orange solid. LRMS (APCI) calc'd for (C$_{14}$H$_6$N$_4$O$_2$S) [M+H]$^+$, 247.0. found 247.0.

Step 5. 5-Chloro-4-(imidazo[1,2-b]pyridazin-3-yl)-1,3-thiazole-2-carbonyl chloride

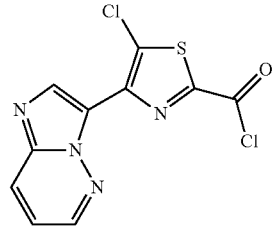 [SMILES: O=C(Cl)c1nc(-c2cnc3cccnn23)c(Cl)s1]

4-(Imidazo[1,2-b]pyridazin-3-yl)-1,3-thiazole-2-carboxylic acid (49 mg, 0.20 mmol) and thionyl chloride (3.0 mL, 41 mmol) were placed in a sealed tube and heated at 80° C. for 42 h. The reaction was cooled to room temperature and concentrated under reduced pressure to give an orange solid. The residue was used immediately in the next step. LRMS (APCI) calc'd for the methyl ester of the title compound (C$_{11}$H$_7$ClN$_4$O$_2$S) [M+H]$^+$, 295.0. found 295.0.

Step 6. N-[(1R,6S)-6-Amino-2,2-difluorocyclohexyl]-5-chloro-4-(imidazo[1,2-b]pyridazin-3-yl)-1,3-thiazole-2-carboxamide

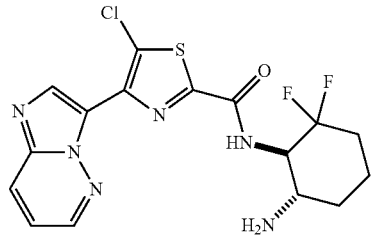

5-Chloro-4-(imidazo[1,2-b]pyridazin-3-yl)-1,3-thiazole-2-carbonyl chloride (59.5 mg, 0.199 mmol) and tert-butyl [(1S,2R)-2-amino-3,3-difluorocyclohexyl]carbamate (54.8 mg, 0.219 mmol) were dissolved in dry dichloromethane (3 mL). The reaction mixture was left to stir at room temperature for 42 h. After consumption of the starting material, trifluoroacetic acid (2 mL) was added to the reaction mixture and left to stir at room temperature for 2 h. The solution was then concentrated and the residue purified by prep HPLC. The compound was neutralized by taking the fractions and adding an aqueous saturated sodium bicarbonate solution and extracting three times with ethyl acetate. The combined organics were dried with magnesium sulfate, filtered, and concentrated to afford the title compound as a yellow solid. $^1$H NMR (500 MHz, CD$_3$SOCD$_3$) δ 8.73 (d, 1H); 8.66 (s, 1H); 8.24 (d, 1H); 7.45 (dd, 1H); 4.05 (m, 1H); 2.85 (m, 1H); 2.08 (m, 1H); 1.22-2.08 (m, 6H). LRMS (APCI) calc'd for (C$_{16}$H$_{15}$ClF$_2$N$_6$OS) [M+H]$^+$, 413.1. found 413.0.

According to Example 28, Example 29 was prepared from 3-bromoimidazo[1,2-a]pyridine.

Example 29

N-[(1R,6S)-6-Amino-2,2-difluorocyclohexyl]-5-chloro-4-(imidazo[1,2-a]pyridin-3-yl)-1,3-thiazole-2-carboxamide

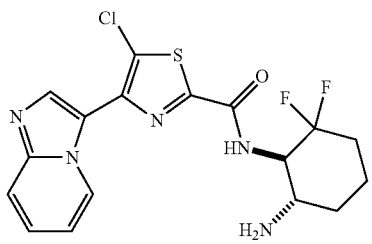

calc'd (M+H)$^+$ 412.1. found (M+H)$^{30}$ 412.0

What is claimed is:

1. A compound of formula I:

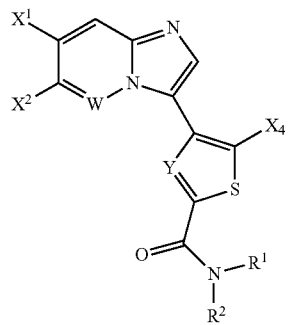

or a pharmaceutically acceptable salt thereof; wherein:
W is =N—;
X$^1$ is selected from the group consisting of: H, halogen, CF$_3$, phenyl, and a monocyclic or bicyclic ring system comprising up to 10 ring atoms, of which 1-3 are selected from N, O and S(O)$_x$ and the remainder are C, said phenyl and ring system bearing 0-3 substituents independently selected from halogen and C$_{1-4}$alkyl, optionally substituted with up to 3 halogen atoms;
X$^2$ is selected from the group consisting of: H, halogen and phenyl bearing 0 to 5 halogen substituents;
X$^4$ is selected from the group consisting of: H, halogen, phenyl-(CH$_2$)$_p$—, C$_{3-6}$cycloalkyl-(CH$_2$)$_q$—, C$_{1-6}$alkyl and C$_{2-6}$alkenyl, said phenyl-(CH$_2$)$_p$—, C$_{3-6}$cycloalkyl-(CH$_2$)$_q$—, C$_{1-6}$alkyl and C$_{2-6}$alkenyl optionally substituted with up to 3 halogen atoms, and p and q are independently 0, 1, 2 or 3;
Y is selected from the group consisting of: =N— and =CH—;
R$^1$ represents H or C$_{1-4}$alkyl which is optionally substituted with OH, CN, CF$_3$, C$_{1-4}$alkoxy, amino, C$_{1-4}$alkylamino or di(C$_{1-4}$alkyl)amino;
R$^2$ is selected from:
(i) H;
(ii) C$_{1-8}$alkyl or C$_{2-8}$alkenyl, either of which optionally bears up to 3 substituents independently selected from halogen, OH, CN, CF$_3$, OR$^3$, SR$^4$, SO$_2$R$^4$, SO$_2$N(R$^3$)$_2$, COR$^3$, CO$_2$R$^3$, CON(R$^3$)$_2$, N(R$^3$)$_2$, NR$^3$COR$^4$, NR$^3$SO$_2$R$^4$ and phenyl, said phenyl bearing 0 to 5 halogen substituents; and
(iii) C$_{3-10}$cycloalkyl, C$_{3-10}$cycloalkylC$_{1-4}$alkyl, Het, HetC$_{1-4}$alkyl, aryl or arylC$_{1-4}$alkyl, any of which optionally bears up to 3 substituents independently selected from halogen, OH, oxo, CN, CF$_3$, R$^4$, OR$^3$, SR$^4$, SO$_2$R$^4$, SO$_2$N(R$^3$)$_2$, COR$^3$, CO$_2$R$^3$, CON(R$^3$)$_2$, N(R$^3$)$_2$, NR$^3$COR$^4$ and NR$^3$SO$_2$R$^4$; where "aryl" refers to phenyl or 5- or 6-membered heteroaryl, either of which phenyl or heteroaryl is optionally fused to a 5- or 6-membered carbocycle or heterocycle, and "Het" refers to a nonaromatic mono- or bicyclic heterocyclic system of up to 10 ring atoms, of which 1-3 are selected from N, O and S(O)$_x$ and the remainder are C;
or R$^1$ and R$^2$ together may complete a mono- or bicyclic heterocyclic system of up to 10 ring atoms which optionally bears up to 3 substituents independently selected from halogen, OH, oxo, CN, CF$_3$, R$^4$, OR$^3$, SR$^4$, SO$_2$R$^4$, SO$_2$N(R$^3$)$_2$, COR$^3$, CO$_2$R$^3$, CON(R$^3$)$_2$, N(R$^3$)$_2$, NR$^3$COR$^4$ and NR$^3$SO$_2$R$^4$;
each R$^3$ independently represents H or C$_{1-6}$alkyl which is optionally substituted with up to 3 halogen atoms or with OH, CN, CF$_3$, C$_{1-4}$alkoxy, amino, C$_{1-4}$alkylamino or di(C$_{1-4}$alkyl)amino, or R$^3$ represents phenyl, benzyl or 5- or 6-membered heteroaryl, any of which optionally bears up to 3 substituents independently selected from halogen, OH, CN, CF$_3$, C$_{1-4}$alkyl, C$_{1-4}$alkoxy, amino, C$_{1-4}$alkylamino and di(C$_{1-4}$alkyl)amino;
or two R$^3$ groups attached to the same nitrogen atom may complete a heterocycle of up to 6 ring atoms which optionally bears up to 3 substituents independently selected from halogen, OH, oxo, CN, CF$_3$, C$_{1-4}$alkyl, C$_{1-4}$alkoxy, amino, C$_{1-4}$alkylamino and di(C$_{1-4}$alkyl)amino;
R$^4$ has the same definition as R$^3$ except that R$^4$ is not H; and
each x is independently 0, 1 or 2.

2. A compound according to claim 1 or a pharmaceutically acceptable salt thereof, wherein Y is =CH—.

3. A compound according to claim 1 or a pharmaceutically acceptable salt thereof, wherein Y is =N—.

4. A compound according to claim 1 or a pharmaceutically acceptable salt thereof, wherein X$^1$ is phenyl bearing 0 to 3 halogen substituents.

5. A compound according to claim 1 or a pharmaceutically acceptable salt thereof, wherein X$^1$ is H.

6. A compound according to claim 1 or a pharmaceutically acceptable salt thereof, wherein X$^1$ is halogen.

7. A compound according to claim 1 or a pharmaceutically acceptable salt thereof, wherein $X^1$ is $CF_3$.

8. A compound according to claim 1 or a pharmaceutically acceptable salt thereof, wherein $X^2$ is H.

9. A compound according to claim 1 or a pharmaceutically acceptable salt thereof, wherein $X^4$ is selected from H, halogen, $C_{1-4}$alkyl bearing 0 to 3 halogen substituents, cyclopropyl, cyclopropylmethyl and benzyl.

10. A compound according to claim 1 or a pharmaceutically acceptable salt thereof, wherein $R^1$ is H.

11. A compound according to claim 1 or a pharmaceutically acceptable salt thereof, wherein $R^2$ is $C_{3-10}$cycloalkyl bearing up to 3 substituents independently selected from halogen, OH, oxo, CN, $CF_3$, $R^4$, $OR^3$, $SR^4$, $SO_2R^4$, $SO_2N(R3)_2$, $COR^3$, $CO_2R^3$, $CON(R^3)_2$, $N(R^3)_2$, $NR^3COR^4$ and $NR^3SO_2R^4$.

12. A compound according to claim 11 or a pharmaceutically acceptable salt thereof, wherein $R^2$ is cyclohexyl bearing up to 3 substituents independently selected from halogen, OH, oxo, CN, $CF_3$, $R^4$, $OR^3$, $SR^4$, $SO_2R^4$, $SO_2N(R^3)_2$, $COR^3$, $CO_2R^3$, $CON(R^3)_2$, $N(R^3)_2$, $NR^3COR^4$ and $NR^3SO_2R^4$.

13. A compound according to claim 1 or a pharmaceutically acceptable salt thereof, wherein:
Y is =CH—;
$X^1$ is selected from the group consisting of: H, halogen, phenyl bearing 0 to 3 halogen substituents and $CF_3$;
$X^2$ is H;
$X^4$ is selected from the group consisting of: H, halogen, $C_{1-4}$alkyl bearing 0 to 3 halogen substituents, cyclopropyl, cyclopropylmethyl and benzyl;
$R^1$ is H; and
$R^2$ is $C_{3-10}$cycloalkyl, $C_{3-10}$cycloalkyl$C_{1-4}$alkyl, Het, Het$C_{1-4}$alkyl, aryl or aryl$C_{1-4}$alkyl, any of which optionally bears up to 3 substituents independently selected from halogen, OH, oxo, CN, $CF_3$, $R^4$, $OR^3$, $SR^4$, $SO_2R^4$, $SO_2N(R^3)_2$, $COR^3$, $CO_2R^3$, $CON(R^3)_2$, $N(R^3)_2$, $NR^3COR^4$ and $NR^3SO_2R^4$; where "aryl" refers to phenyl or 5- or 6-membered heteroaryl, either of which phenyl or heteroaryl is optionally fused to a 5- or 6-membered carbocycle or heterocycle, and "Het" refers to a nonaromatic mono- or bicyclic heterocyclic system of up to 10 ring atoms, of which 1-3 are selected from N, O and $S(O)_x$ and the remainder are C.

14. A compound according to claim 1 or a pharmaceutically acceptable salt thereof, wherein:
Y is =N—;
$X^1$ is selected from the group consisting of: H, halogen, phenyl bearing 0 to 3 halogen substituents and $CF_3$;
$X^2$ is H;
$X^4$ is selected from the group consisting of: H, halogen, $C_{1-4}$alkyl bearing 0 to 3 halogen substituents, cyclopropyl, cyclopropylmethyl and benzyl;
$R^1$ is H; and
$R^2$ is $C_{3-10}$cycloalkyl, $C_{3-10}$cycloalkyl$C_{1-4}$alkyl, Het, Het$C_{1-4}$alkyl, aryl or aryl$C_{1-4}$alkyl, any of which optionally bears up to 3 substituents independently selected from halogen, OH, oxo, CN, $CF_3$, $R^4$, $OR^3$, $SR^4$, $SO_2R^4$, $SO_2N(R^3)_2$, $COR^3$, $CO_2R^3$, $CON(R^3)_2$, $N(R^3)_2$, $NR^3COR^4$ and $NR^3SO_2R^4$; where "aryl" refers to phenyl or 5- or 6-membered heteroaryl, either of which phenyl or heteroaryl is optionally fused to a 5- or 6-membered carbocycle or heterocycle, and "Het" refers to a nonaromatic mono- or bicyclic heterocyclic system of up to 10 ring atoms, of which 1-3 are selected from N, O and $S(O)_x$ and the remainder are C.

15. A compound selected from the group consisting of:
N-[6-amino-2,2-difluorocyclohexyl]-4-(imidazo[1,2-b]pyridazin-3-yl)-5-methylthiophene-2-carboxamide;
cis-2-({[4-(imidazo[1,2-b]pyridazin-3-yl)thiophen-yl]carbonyl}amino)cyclohexanaminium trifluoroacetate;
N-[cis-2-aminocyclohexyl]-4-[7-(4-fluorophenyl)imidazo[1,2-b]pyridazin-3-yl]thiophene-2-carboxamide;
N-[6-amino-2,2-difluorocyclohexyl]-4-(imidazo[1,2-b]pyridazin-3-yl)thiophene-2-carboxamide;
4-[7-(4-fluorophenyl)imidazo[1,2-b]pyridazin-3-yl]-N-(2,2,2-trifluoroethyl)thiophene-2-carboxamide;
N-[6-amino-2,2-difluorocyclohexyl]-4-(7-(4-fluorophenyl)imidazo[1,2-b]pyridazin-3-yl)thiophene-2-carboxamide;
N-[(cis-4-amino-1,1-dioxidotetrahydro-2H-thiopyran-3-yl]-4-(imidazo[1,2-b]pyridazin-3-yl)-5-methylthiophene-2-carboxamide;
N-[cis-3-amino-1,1-dioxidotetrahydro-2H-thiopyran-4-yl]-4-(imidazo[1,2-b]pyridazin-3-yl)-5-methylthiophene-2-carboxamide;
N-[cis-2-aminocyclopentyl]-4-(imidazo[1,2-b]pyridazin-3-yl)thiophene-2-carboxamide;
N-[6-amino-2,2-difluorocyclohexyl]-5-ethyl-4-(imidazo[1,2-b]pyridazin-3-yl)thiophene-2-carboxamide;
N-[6-amino-2,2-difluorocyclohexyl]-5-benzyl-4-(imidazo[1,2-b]pyridazin-3-yl)thiophene-2-carboxamide;
N-[6-amino-2,2-difluorocyclohexyl]-4-(imidazo[1,2-b]pyridazin-3-yl)-5-(prop-1-en-2-yl)thiophene-2-carboxamide;
N-[6-amino-2,2-difluorocyclohexyl]-5-cyclopropyl-4-(imidazo[1,2-b]pyridazin-3-yl)thiophene-2-carboxamide;
N-[6-amino-2,2-difluorocyclohexyl]-5-ethyl-4-[7-(trifluoromethyl)imidazo[1,2-b]pyridazin-3-yl]thiophene-2-carboxamide;
N-[6-amino-2,2-difluorocyclohexyl]-5-(difluoromethyl)-4-(imidazo[1,2-b]pyridazin-3-yl)thiophene-2-carboxamide; and
N-[6-amino-2,2-difluorocyclohexyl]-5-chloro-4-(imidazo[1,2-b]pyridazin-3-yl)-1,3-thiazole-2-carboxamide;
and pharmaceutically acceptable salts of any of the foregoing compounds.

16. A pharmaceutical composition comprising a compound of formula I as defined in claim 1 or a pharmaceutically acceptable salt thereof, and a pharmaceutically acceptable carrier.

17. A method for treating Alzheimer's disease in a human patient, said method comprising administering to said patient an effective amount of a compound of formula I as defined in claim 1 or a pharmaceutically acceptable salt thereof.

* * * * *